US009642779B2

(12) United States Patent
Elia et al.

(10) Patent No.: US 9,642,779 B2
(45) Date of Patent: May 9, 2017

(54) CLOSED LOOP SYSTEMS AND METHODS FOR OPTIMAL ENTERAL FEEDING AND A PERSONALIZED NUTRITION PLAN

(71) Applicant: ART Healthcare Ltd., Ashkelon (IL)

(72) Inventors: Liron Elia, Kiryat-Ata (IL); Gavriel J. Iddan, Haifa (IL)

(73) Assignee: ART Healthcare Ltd., Natania (IL)

( * ) Notice: Subject to any disclaimer, the term of this patent is extended or adjusted under 35 U.S.C. 154(b) by 0 days.

(21) Appl. No.: 14/952,968

(22) Filed: Nov. 26, 2015

(65) Prior Publication Data

US 2016/0143817 A1 May 26, 2016

Related U.S. Application Data

(60) Provisional application No. 62/084,614, filed on Nov. 26, 2014.

(51) Int. Cl.
*A61J 15/00* (2006.01)
*G06F 19/00* (2011.01)

(52) U.S. Cl.
CPC ....... *A61J 15/0084* (2015.05); *A61J 15/0088* (2015.05); *G06F 19/3406* (2013.01); *A61J 15/0003* (2013.01); *A61J 15/0015* (2013.01)

(58) Field of Classification Search
CPC .................................................. A61J 15/0084
See application file for complete search history.

(56) References Cited

U.S. PATENT DOCUMENTS

| 2008/0097179 A1 | 4/2008 | Russo |
| 2009/0275824 A1 | 11/2009 | Cholette |
| 2010/0030133 A1* | 2/2010 | Elia ........................ A61B 5/037 604/28 |

(Continued)

FOREIGN PATENT DOCUMENTS

| WO | WO 97/35622 | 10/1997 |
| WO | WO 2016/084090 | 6/2016 |

OTHER PUBLICATIONS

TV Moreira, M McQuiggan. Methods for the Assessment of Gastric Emptying in Critically Ill, Enterally Fed Adults. Nutrition in Clinical Practice. 2009, vol. 24, No. 2, p. 261-273.*

(Continued)

*Primary Examiner* — John S Brusca
*Assistant Examiner* — Olivia Wise

(57) ABSTRACT

There is provided a computer-implemented method for calculating a gastric emptying rate from a stomach lumen into a small intestine of a patient, comprising: using at least one processor for executing the following during an enteral tube feeding of a stomach of the patient by a feeding mechanism: analyzing outputs of at least one stomach sensor located within the stomach for detecting a stop feeding condition; pausing the enteral tube feeding in response to a detection of the stop feeding condition; after a predefined period of time, restarting the enteral tube feeding until the stop condition is redetected by an analysis of said outputs; calculating a gastric emptying rate based on an amount of feeding content delivered during a period between the restarting and the redetection; and instructing the feeding mechanism to adapt a feeding rate of the enteral tube feeding according to the gastric emptying rate.

16 Claims, 17 Drawing Sheets
(10 of 17 Drawing Sheet(s) Filed in Color)

(56) References Cited

U.S. PATENT DOCUMENTS

2013/0158514 A1 6/2013 Elia et al.
2014/0058352 A1* 2/2014 Francis ............... G06F 19/3468
   604/503

OTHER PUBLICATIONS

NT Williams, Medication administration through enteral feeding tubes. Am J Health-Syst Pharm, Dec. 15, 2008, vol. 65, p. 2347-2357.*

J Reignier, E Mercier, A Le Gouge, T Boulain, A Desachy, F Bellec, M Clavel, JP Frat, G Plantefeve, JP Quenot, JB Lascarrou. Effect of Not Monitoring Residual Gastric Volume on Risk of Ventilator-Associated Pneumonia in Adults Receiving Mechanical Ventilation and Early Enteral Feeding. JAMA, Jan. 16, 2013, vol. 309, No. 3, p. 249-256.*

International Search Report and the Written Opinion Dated Mar. 6, 2016 From the International Searching Authority Re. Application No. PCT/IL2015/051156.

* cited by examiner

FIG. 10

| | | Description/ Indication | ENERGY kcal/mL | PROTEIN %energy | FAT %energy | CARBOHYDRATE %energy | OSMOLALITY mOsm/kg |
|---|---|---|---|---|---|---|---|
| STANDARD FEEDS<br>May or may not contain fibre; fibre-enriched formulae have fibre content approx. 10-15g/L | Standard feeds | No special requirements | 1.0-1.2 | 16% | 30% | 55% | 300-500 |
| | High-protein standard feeds | Increased protein requirement | 1.0-1.2 | 20% | 30% | 50% | 300-500 |
| | High energy feeds (1.5kcal/mL) | High energy needs, or fluid restriction | 1.5 | 20% | 30% | 50% | 500-650 |
| | High energy feeds (2kcal/mL) | High energy needs, or fluid restriction | 2.0 | 15% | 40% | 45% | 450-800 |
| PRE-DIGESTED FORMULAE<br>Nutrients in their simple form (protein as peptides or free amino acids, carbohydrate as monosaccharides, low in fat, may contain MCT). | Semi-elemental | Minimal residue, protein as peptides | 1.0 | 20% | 10% | 70% | 320-520 |
| | Elemental | Minimal residue, protein as free amino acids. | 1.0 | 15-20% | 3-15% (varies widely between products) | 70-85% | 500-730 |
| RENAL FORMULAE<br>Energy dense, reduced fluid and electrolyte content. Modified protein content. | Moderate protein | Restricted fluid and electrolytes | 2.0 | 18% | 45% | 40% | 650-700 |
| | Low protein | End-stage renal failure, not for dialysis | 2.0 | 3%-10% | 45-50% | 45-50% | 450-650 |

CLOSED LOOP SYSTEMS AND METHODS FOR OPTIMAL ENTERAL FEEDING AND A PERSONALIZED NUTRITION PLAN

RELATED APPLICATION

This application claims the benefit of priority under 35 USC 119(e) of U.S. Provisional Patent Application No. 62/084,614 filed on Nov. 26, 2014, the contents of which are incorporated herein by reference in their entirety.

BACKGROUND

The present invention, in some embodiments thereof, relates to enteral feeding and, more specifically, but not exclusively, to systems and methods that control enteral feeding.

Patients requiring enteral feeding (i.e., feeding via a tube inserted into the stomach) include, for example, babies, patients in the intensive care unit (ICU) which might be sedated and/or intubated, and patients otherwise unable to swallow or ingest food in the normal manner. The tube is inserted into the stomach (or duodenum, or jejunum, or other locations in the digestive track) via the nose, the mouth, or a surgically created opening.

Feeding rate is of prime importance in the patient management and his/her recuperation. However, feeding overdose will result reflux ending with aspiration pneumonia and should be prevented at all cost. These are contradicting requirements, the desire to maximize feeding for enhancing recuperation on one hand and the need to prevent reflux on the other hand.

One method of making decisions regarding enteral feeding involves manually measuring the volume of fluid in the patient's stomach after an enteral feeding session, by using a syringe to aspirate the stomach contents. The measured volume is termed Gastric Residual Volume (GRV). The value of the GRV is used by healthcare professional to decide, for example, if the patient received enough food, is having problems ingesting the delivered food, and/or if the patient is at increased risk of aspiration pneumonia. For example, when the measured GRV is above a threshold, the next enteral feeding is delayed. A full assessment using GRV may take up to 72 hours, with 4 hour intervals between GRV measurements.

SUMMARY

According to an aspect of some embodiments of the present invention there is provided a computer-implemented method for calculating a gastric emptying rate from a stomach lumen into a small intestine of a patient, comprising: using at least one processor for executing the following during an enteral tube feeding of a stomach of the patient by a feeding mechanism: analyzing outputs of at least one stomach sensor located within the stomach for detecting a stop feeding condition; pausing the enteral tube feeding in response to a detection of the stop feeding condition; after a predefined period of time, restarting the enteral tube feeding until the stop condition is redetected by an analysis of said outputs; calculating a gastric emptying rate based on an amount of feeding content delivered during a period between the restarting and the redetection; and instructing the feeding mechanism to adapt a feeding rate of the enteral tube feeding according to the gastric emptying rate.

Optionally, the method further comprises receiving a personalized nutrition plan including a target fluid delivery rate; performing the enteral tube feeding according to the target fluid delivery rate; and adapting the target fluid delivery rate according to the calculated gastric emptying rate. Optionally, the method further comprises automatically adjusting the personalized nutrition plan by adjusting the target fluid delivery rate to match the target fluid delivery rate within a tolerance.

Optionally, the method further comprises transmitting an alert message for presentation on a display of a mobile device when the target fluid delivery rate is different than the calculated gastric emptying rate based on a tolerance. Optionally, the method further comprises presenting a suggestion to administer gastroprokinetic medication on a display when the target fluid delivery rate is higher than the calculated gastric emptying rate based on a tolerance. Optionally, the target fluid delivery rate includes different values defined according to a time of day.

Optionally, the method further comprises presenting within a GUI presented on a display, at least one field for allowing a user to select or enter at least one patient parameter; calculating a plurality of feeding options according to the at least one patient parameter; presenting the plurality of feeding options within the graphical user interface (GUI); receiving a selection of at least one of the plurality of feeding options from a user using the GUI; and calculating the personalized nutrition plan and target fluid delivery rate based on the received selection. Optionally, the at least one patient parameter includes at least one member selected from the group consisting of: gender, age, height, weight, diet restrictions, acute medical condition, and chronic medical condition. Optionally, the plurality of feeding options include at least one member selected from the group consisting of: calories, protein amount, method of calculation, and available formulas.

Optionally, fluid is delivered during the period of time according to the target fluid delivery rate, and the gastric emptying rate is calculated based on the fluid delivered during the period of time.

Optionally, the predefined period of time is selected to correspond to an estimated amount of time expected for the stomach of the patient to empty itself of a fluid meal.

Optionally, the predefined period of time is automatically determined based on an analysis of signals received from stomach activity sensors located in the stomach indicative of a stomach emptying event. Optionally, the stomach emptying event is automatically detected by identifying at least one signal pattern correlated with stomach peristalsis activity associated with the stomach emptying event.

Optionally, the calculating is performed using the equation: $q = Q/(T+t)$ wherein: q denotes the gastric emptying rate; Q denotes the volume of fluid needed to fill the stomach from a first sensor Z1 representing a low fluid level to a second sensor Z2 representing a high fluid level; T denotes the elapsed gastric emptying time from fluid level Z2 to Z1; and t denotes the filling make up time. Optionally, when fluid reaches Z2 feeding is paused for a time period T, then feeding is resumed until level Z2 is reached and the time t is measured.

According to an aspect of some embodiments of the present invention there is provided a computer-implemented method for feeding a patient using a tube located in a stomach of the patient, comprising: monitoring a fluid delivery rate of fluid delivered to a patient using a tube located in a stomach of the patient; receiving at least one signal from at least one sensor located within the stomach, the at least one sensor measuring stomach activity associated with stomach muscle movement; analyzing the at least one signal to detect a signal pattern indicative of a stomach evacuation event; and adjusting the fluid delivery rate according to the detected signal pattern.

Optionally, the analyzing comprises correlating the at least one signal to a stored signal pattern associated with a stomach evacuation event.

According to an aspect of some embodiments of the present invention there is provided a system for calculating a gastric emptying rate from a stomach lumen into a small intestine of a patient, comprising: a control unit, comprising: an output interface; a sensor interface that receives at least one signal from at least one stomach sensor located within a stomach lumen of a patient; a program store storing code; and a processor coupled to the sensor interface, the output interface, and the program store for implementing the stored code, the code comprising: code to analyze outputs of the at least one stomach sensor for detecting a stop feeding condition, pause enteral tube feeding in response to a detection of the stop feeding condition, after a predefined period of time restart the enteral tube feeding until the stop condition is redetected by an analysis of said outputs, calculate a gastric emptying rate based on an amount of feeding content delivered during a period between the restarting and the redetection; and instruct the feeding mechanism to adapt a feeding rate of the enteral tube feeding according to the gastric emptying rate.

Optionally, the at least one stomach sensors include at least one impedance sensor and the at least one signal includes at least one impedance measurement.

Optionally, the at least one stomach sensor includes at least one fluid sensor disposed along a distal end portion of an enteral feeding tube positioned in the stomach of the patient such that the at least one fluid sensor is located within the stomach in proximity to the lower esophageal sphincter, and the at least one signal denotes the presence of fluid in proximity to the respective sensor at a respective position along the tube.

Optionally, the system further comprises a graphical user interface (GUI) application installed on a client terminal in communication with the control unit through a network interface, the GUI application allowing a user to enter at least one patient parameter; code to determine a personalized nutrition plan including a target fluid delivery rate based on the at least one patient parameter, compare the target fluid delivery rate to the calculated gastric emptying rate, and adjust the personalized nutrition plan by adjusting the target fluid delivery rate to match the target fluid delivery rate within a tolerance.

According to an aspect of some embodiments of the present invention there is provided a computer-implemented method for calculating a gastric emptying rate from a stomach lumen into a small intestine of a patient, comprising: receiving, from each of a plurality of stomach sensors located within a stomach lumen of a patient, at least one signal; identifying a pattern indicative of a gastric emptying rate from the stomach lumen to a small intestine of the patient based on an analysis of the at least one signal received from each of the plurality of sensors; calculating the gastric emptying rate based on the identified pattern; and outputting an indication of the gastric emptying rate.

Optionally, the identified pattern comprises a fluid level of fluid in the stomach lumen determined according to which at least one sensor of the plurality of sensors detect the presence of fluid or air.

Optionally, the identified pattern comprises a change in a fluid level in the fluid in the stomach lumen over a period of time determined according to at least one sensor of the plurality of sensors detecting a change in the presence of fluid or air.

Optionally, the method further comprises detecting a stomach emptying event based on the identified pattern. Optionally, calculating comprises calculating the gastric emptying rate for the time duration of the stomach emptying event.

Optionally, the pattern is indicative of a volume of fluid in the stomach, and calculating the gastric emptying rate is based on detecting changes in fluid volume in the stomach lumen over a period of time.

Optionally, the pattern is indicative of a member selected from the group consisting of: emptying of the stomach of an enterally delivered food dose, stomach empty and in a state ready for a next enterally delivered food dose, delayed emptying of the stomach of the enterally delivered food, and stomach is filling up with enterally delivered food.

Optionally, the method further comprises receiving from a flow sensor located external to the body of the patient, at least one signal indicative of a flow rate of fluid entering the stomach lumen; and calculating comprises calculating the gastric emptying rate based on the identified pattern and received flow rate.

Optionally, the method further comprises comparing the gastric emptying rate according to a target fluid delivery rate; and outputting instructions to dynamically adjust a flow rate of fluid entering the stomach lumen from an external source according to the comparison.

Optionally, the method further comprises comparing the gastric emptying rate according to a measured flow rate of fluid entering the stomach lumen; and automatically generating instructions to dynamically adjust the flow rate of fluid to match the gastric emptying rate. Optionally, dynamically adjusting comprises dynamically matching the flow rate of fluid entering the stomach lumen to the calculated gastric emptying rate.

Optionally, the method further comprises monitoring at least one of a fluid level and a volume of fluid in the stomach lumen based on the identified pattern; and comparing the monitored at least one of fluid level and volume of fluid according to a target threshold or target range of at least one of fluid level and fluid volume in the stomach lumen; and outputting instructions to dynamically adjust a flow of fluid entering the stomach lumen from an external source according to the comparison.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

The patent or application file contains at least one drawing executed in color. Copies of this patent or patent application publication with color drawing(s) will be provided by the Office upon request and payment of the necessary fee.

In the drawings:

FIG. 1A is a flowchart of a method for calculating a gastric emptying rate from a stomach lumen into a small intestine of a patient, in accordance with some embodiments of the present invention;

FIG. 1B is a flowchart of another method for calculating the gastric emptying rate, in accordance with some embodiments of the present invention;

FIG. 2 is a block diagram of a system that calculates a gastric emptying rate from a stomach lumen into a small intestine of a patient, in accordance with some embodiments of the present invention, without the need for GRV;

FIG. 3 is a schematic of an exemplary feeding bag system for delivery of fluid to the stomach of the patient, including a tube, flow sensor(s) for measuring the rate and/or volume of delivered fluid, and/or a flow control mechanism for controlling the rate and/or volume of delivered fluid, in accordance with some embodiments of the present invention;

FIG. 4 is a schematic of an exemplary pinch valve as an exemplary embodiment implementation of a fluid control mechanism for controlling the rate of fluid flowing through the feeding bag tube into the stomach of a patient, in accordance with some embodiments of the present invention;

FIG. 5 is an exemplary recording of stomach activity recorded over several hours, in accordance with some embodiments of the present invention;

FIG. 6 is a pattern identified from the recording of FIG. 5, in accordance with some embodiments of the present invention;

FIG. 7 is a schematic depicting a gastric emptying pattern based on fluid level in the stomach, and/or changes in the fluid level, in accordance with some embodiments of the present invention;

FIG. 8 is a flowchart of an exemplary method for generating an indication for administration of prokinetics drugs, in accordance with some embodiments of the present invention;

FIG. 9 is a flowchart of an exemplary method for automatic generation of the personalized nutrition regimen, in accordance with some embodiments of the present invention;

FIG. 10 is a table of nutrition data for generation of the personalized nutrition regimen, in accordance with some embodiments of the present invention;

Figure 11:
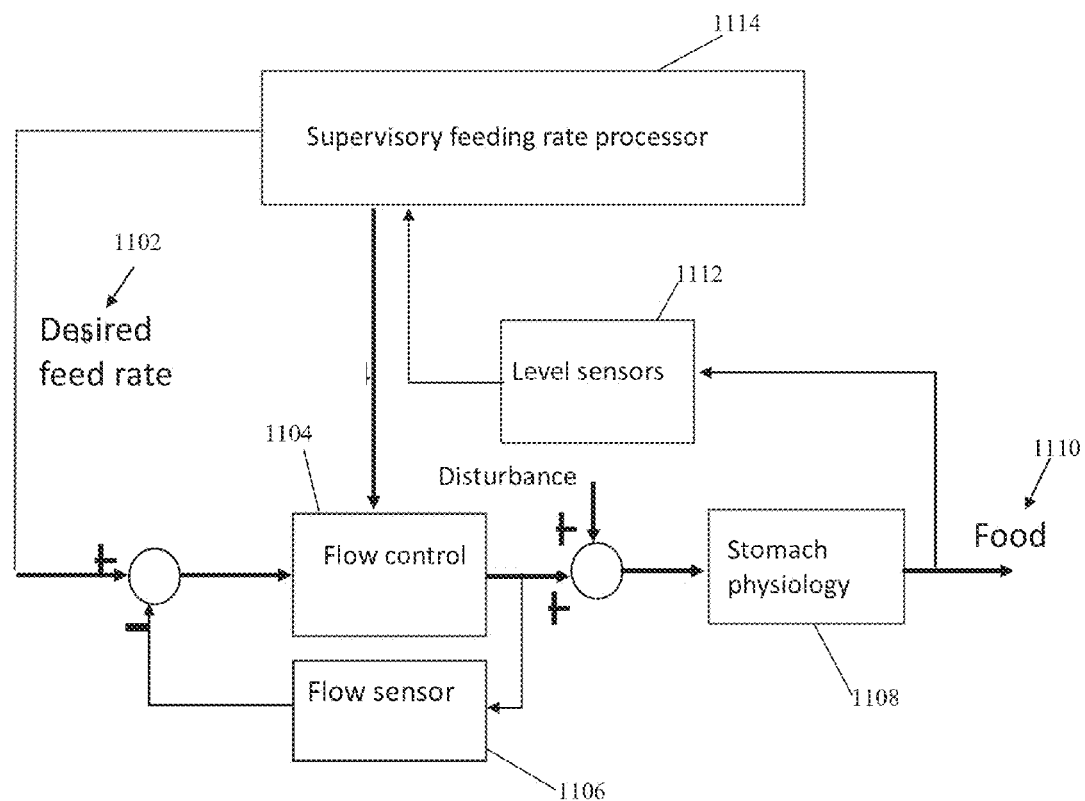
Figure 12:
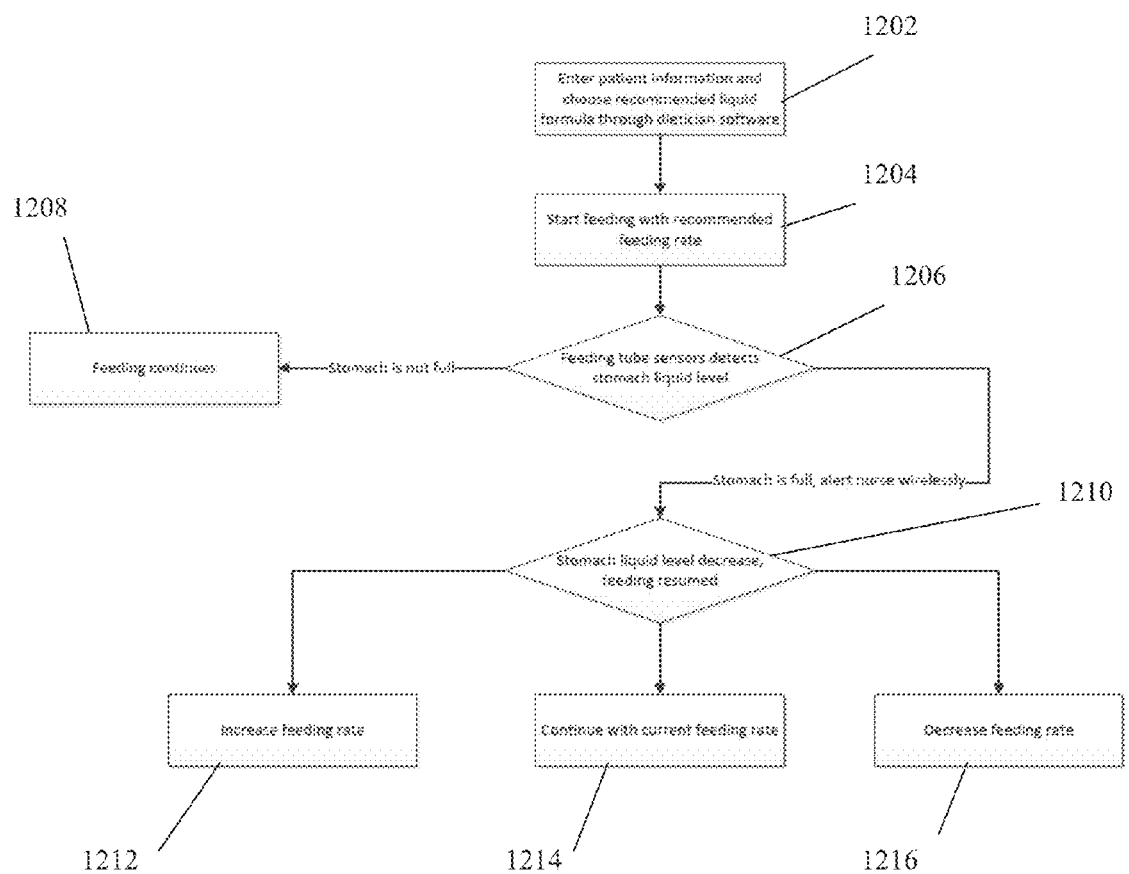

FIG. 11 is a dataflow diagram for dynamic adjustment of the rate of fluid delivered to the stomach of the patient according to the calculated gastric emptying rate, in accordance with some embodiments of the present invention;

FIG. 12 is a flowchart of another method for dynamic adjustment of the rate of fluid delivered to the stomach of the patient using the systems and/or methods described herein, in accordance with some embodiments of the present invention; and FIGS. 13A-13D are exemplary GUI screens for allowing a healthcare worker to enter patient parameters for automatic determination of the personalized nutrition plan, in accordance with some embodiments of the present invention.

DETAILED DESCRIPTION

The present invention, in some embodiments thereof, relates to enteral feeding and, more specifically, but not exclusively, to systems and methods that control enteral feeding.

An aspect of some embodiments of the present invention relates to systems and/or methods, optionally a processor implementing code, for calculating a gastric emptying rate and/or detect events of stomach emptying for an enterally fed patient (e.g., via a nasogastric tube, or other tube). The calculated gastric emptying rate is indicative of the rate that the stomach of the patient empties its contents (which include nutrition delivered via the tube) out of the stomach, via the pylorus into the duodenum and other parts of the small intestine. The detected stomach emptying event is indicative of the state of the stomach in which the stomach is emptying its contents into the small intestine (e.g., peristalsis). The detected stomach emptying event(s) may be included within the calculated gastric emptying rate. For example, the gastric emptying rate may be calculated for the duration of the stomach emptying event, indicating the volume and/or rate at which fluid leaves the stomach during the stomach emptying event. In the example, the gastric emptying rate may be assumed to be zero (or close to zero) when the stomach emptying event is not occurring (e.g., stomach is not emptying). The gastric emptying rate is calculated using signals received from stomach sensors located within the stomach, optionally spaced apart along the distal end portion of the tube. The stomach sensors may measure impedance and/or peristaltic movement of the stomach. A pattern indicative of the gastric emptying rate is identified based on the signals, for example, indicative of a level and/or change in level of fluid in the stomach, indicative of a volume and/or change in volume of fluid in the stomach, and/or indicative of postprandial—a feeding session, peristalsis. The gastric emptying rate is calculated and/or the stomach emptying event is detected based on the identified pattern, and outputted.

The systems and/or methods described herein operate in a closed loop manner. A fluid delivery rate is selected for feeding the patient using the tube. The gastric emptying rate is calculated. The fluid delivery rate may be adjusted according to the gastric emptying rate, optionally matched to the gastric emptying rate which represents the real-time ability of the patient to safety ingest the food (i.e., reducing risk of aspiration pneumonia). Suggestions for feeding may be automatically generated and presented on a GUI for selection by a user. The systems and/or methods described herein may be viewed as a closed loop control system with a set point adjusted to maintain stomach fluid level within a desired level, thus preventing reflux and delivering the patient stomach emptying rate for optimal feeding calculation.

Optionally, the pattern is indicative of the level of fluid in the stomach (referred to herein as fluid level). The level of fluid may be detected by an analysis of signals received from multiple spaced apart stomach sensors, which may be disposed along the distal end portion of the tube. Sensors below the fluid level (i.e., surrounded by fluid) generate a first type of signal or signal level which may be indicative of the presence of fluid (e.g., relatively low impedance value). Sensors above the fluid level (e.g., surrounded by air) generate a second type of signal which may be indicative of the presence of air (e.g., relatively high impedance value). The fluid level may be determined according to the sensor(s) at which the first signal type transitions into the second signal type. Alternatively or additionally, the pattern is indicative of a change in the fluid level in the stomach. The fluid level may increase or decrease. The change in fluid level, which may be measured as a function of time, may be detected by analyzing the signals received from the stomach sensors, for example, a sensor generating the first signal type that changes to the second signal type may indicate a decrease in the fluid level. The gastric emptying rate may be calculated based on the fluid level and/or change in fluid level, as described herein.

The gastric emptying rate may be indicative of intake over a time range, such as based on a set of measurements performed over time. Gastric residual volume (GRV) test is the standard of care for checking gastric emptying, for example with a feeding rate of 125 cc/hour after 4 hours 500 cc administrated. Now the nurse disconnect the feeding bag from the feeding tube and start suction, if the total amount suctioned is above 200 cc the patient suffers from gastroparesis. Next step is lowering the hourly rate and after 48-72 hours the attending will decide on prokinetic drugs to help with digestion the problem with this practice it's not real-time detection and feedback of stomach activities and by the time becomes aware of the gastroparesis it might be too late—the patient cam get aspiration pneumonia from over-feeding. Also this is a huge waste in nurse time resources and feeding material waste. The systems and/or methods described herein operate without the need for measuring GRV, by dynamically measure the amount and/or rate that the patient is being fed at, and automatically adjust the feeding amount and/or rate, optionally to the rate the patient is actually able to intake into the intestine from the stomach by gastric emptying.

Optionally, the gastric emptying rate is indicative of emptying of the stomach from tube delivered nutrients, for example, when the intestines have adequate motility to empty the fluid. Alternatively, the gastric emptying rate is indicative of the stomach filling up with the tube delivered foods, such as due to lack of sufficient emptying of the stomach, for example, when intestinal motility is depressed (e.g., due to infection, surgery, and/or drugs such as sedatives).

Optionally, the feeding material/fluids delivery-rate is calculated in view of signals received from a flow sensor measuring the flow rate of the fluid entering the feeding tube and then the stomach of the patient. For example, when the identified pattern from the stomach sensors indicates a stable (e.g. within a margin of error) stomach fluid level, and the flow rate measured by the flow sensor is 150 mL/hour, the gastric emptying rate is determined to match (i.e. within a margin of error) the flow rate.

Optionally, the systems and/or methods operate by selecting a level sensor on the feeding tube, and adjusting the feeding rate to maintain the selected level using a closed loop control, to achieve a steady state flow rate for fluid delivery that matches the gastric emptying rate.

Optionally, the calculated gastric emptying rate is compared to the measured flow rate of the fluid entering the stomach of the patient. The calculated gastric emptying rate is indicative of the actual (e.g., real-time) ability of the digestive system of the patient to empty the stomach contents into the small intestine, and further process the food. The calculated gastric emptying rate may change, for example, during different times in the day, be affected by medications (e.g., sedatives), and/or by other events such as infections and/or surgery. When the calculated gastric emptying rate is different than the flow rate (e.g., statistically different, and/or according to a different requirement), instructions may be automatically generated to adjust the flow rate to match the calculated gastric emptying rate. The instructions may be provided to a flow-control mechanism for dynamic and automatic adjustment. In this manner, the delivery of nutrients to the patient is dynamically adjusted to match the actual ability of the patient to process the food.

Alternatively or additionally, the calculated gastric emptying rate is compared to a target fluid delivery rate, for example, selected based on a recommended daily nutrient intake for the patient and/or customized nutrition regimen. When the differences between the rates is substantially different, such as greater than a tolerance, (e.g., statistically significant and/or according to a difference requirement), instructions may be generated to adjust the flow rate of the fluid entering the stomach. The adjustment may be performed automatically and dynamically, for example, by transmitting the instructions to the flow-control mechanism. The adjustment may help ensure that the patient is actually receiving the intended nutrients, for example, helping ensure that the patient receives the full daily nutrient requirements.

Alternatively or additionally, the level and/or volume of fluid in the stomach is monitored based on the calculated gastric emptying rate. The level and/or volume is monitored against a target requirement (e.g., threshold or range) representing the allowed (or maximum) level and/or volume in the stomach. When the level and/or volume meets or exceeds the target requirement, instructions to automatically and dynamically reduce (or stop) the fluid entering the stomach are transmitted to the flow-control mechanism. The target requirement may be selected to reduce aspiration pneumonia, for example, based on experimental evidence and/or best practice, for example, about 150 mL, or about 300 mL, or about 500 mL, or other values.

An aspect of some embodiments of the present invention relates to systems and/or methods for calculating a gastric emptying rate, by analyzing outputs of a stomach sensor located within a stomach, during delivery of fluid to the stomach, to detect a stop feeding condition. The feeding is paused in response to the detected stop feeding condition. The stop feeding condition may be detected when a stomach sensor located within the upper portion of the stomach (e.g., close to the lower esophageal sphincter) senses a change of level of the fluid (like a dipstick mechanism), indicating that the stomach is full (or mostly full) of fluid. A period of time is allowed to elapse, optionally without introducing additional fluid. Fluid delivery (i.e., feeding) is resumed after the period of time (following a drop in the fluid level), and the stop feeding condition is redetected. The gastric emptying rate is calculated based on the amount of fluid delivered to the patient between the restart of the feeding and the redetection of the stop feeding condition. The feeding rate is adapted according to the gastric emptying rate, optionally to match the fluid delivery rate.

Optionally, a personalized nutrition plan is automatically generated for the patient based on patient parameters, which may be automatically obtained by access an electronic medical record of the patient, and/or manually entered by a user using a graphical user interface. The personalized nutrition plan includes a target fluid delivery rate for delivery of fluid to the patient. When the calculated gastric emptying rate is different than the target fluid delivery rate (e.g., within a tolerance), the target fluid delivery rate may be adjusted (automatically or manually) to match the gastric emptying rate.

An aspect of some embodiments of the present invention relates to a computer implemented method for feeding a patient using at tube located in the stomach of the patient, by monitoring fluid delivery to the stomach using the tube, and analyzing signals received from sensor(s) located in the stomach to detect a stomach evacuation event indicating that at least some of the fluid in the stomach entered the intestine. The fluid delivery is adjusted according to the detected stomach evacuation event, for example, additional fluid is delivered when stomach evacuation events are detected.

Optionally, the signals are analyzed to detect stomach peristalsis, using signals measured from electrical and/or mechanical sensors that measure stomach muscle movement. The signals may be analyzed by identifying a correlation with a stored signal pattern associated with a stomach emptying event.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term stomach lumen (or stomach) is meant to include other locations in the digestive tract in which tubes delivering enteral nutrition may be placed in patients, for example, the duodenum, the jejunum, and other locations. As used herein, the term tube means a tube used to deliver nutrients (e.g., fluid, feeding material, enteral nutrition) to the stomach lumen, for example, a nasogastric (NG) tube, an nasojejunal (NJ) tube, and percutaneous endoscopic gastrostomy (PEG) tube.

As used herein, the term fluid is meant to include enteral nutrients delivered to the stomach of the patient, for example, foods in liquid form, water, protein, carbohydrates, fat, mineral, and vitamins.

As used herein, the term gastric emptying rate means a rate calculated over a period of time (for example, approximately instantaneously, over an hour, over 4 hours, over 8 hours, over one day, over 3 days, or other time periods). The gastric emptying rate refers to the rate at which the stomach of the patient empties itself (further into the digestive tract, into the small intestine) of contents that mostly include enteral fluids provided using the tube. The gastric emptying rate may include other body sections, for example, stomach acids, and saliva.

As used herein, the term stomach emptying event means a period of time during which the stomach empties its contents into the intestine. The terms gastric emptying rate and stomach emptying event may sometimes be interchanged. For example, detection of the time interval during which the stomach emptying event occurs may be used for calculation of the gastric emptying rate. The terms gastric emptying rate and stomach emptying event may sometimes be included within one another, for example, calculation of the gastric emptying rate may include detection of the stomach emptying event. It is noted that the different terms result from the fact that stomach emptying is not a continuous process but appears as a bolus type process, while the feeding rate for the patient is based on the time average phenomena.

As used herein, the term flow rate, or flow rate of fluid entering the stomach, or feeding rate means the rate of fluid flowing into the stomach through the tube.

As used herein, the term stomach fluid level, or stomach fluid volume means the calculated volume and/or level of fluid in the stomach. The stomach fluid level may remain decrease, for example, when the stomach is emptying itself and/or when the gastric emptying rate is larger than the flow rate of fluid entering the stomach, which may occur, for example, due to under-feeding, and/or may occur after a feeding session. The stomach fluid level may increase, for example, when the gastric emptying rate is smaller than the flow rate of fluid entering the stomach, which may occur during over-feeding and/or decreased peristalsis and/or decreased gastric emptying activity. The stomach fluid level may remain substantially unchanged (e.g., within a margin of error), for example, when the flow rate is adjusted to match the gastric emptying rate.

Figure 1A:
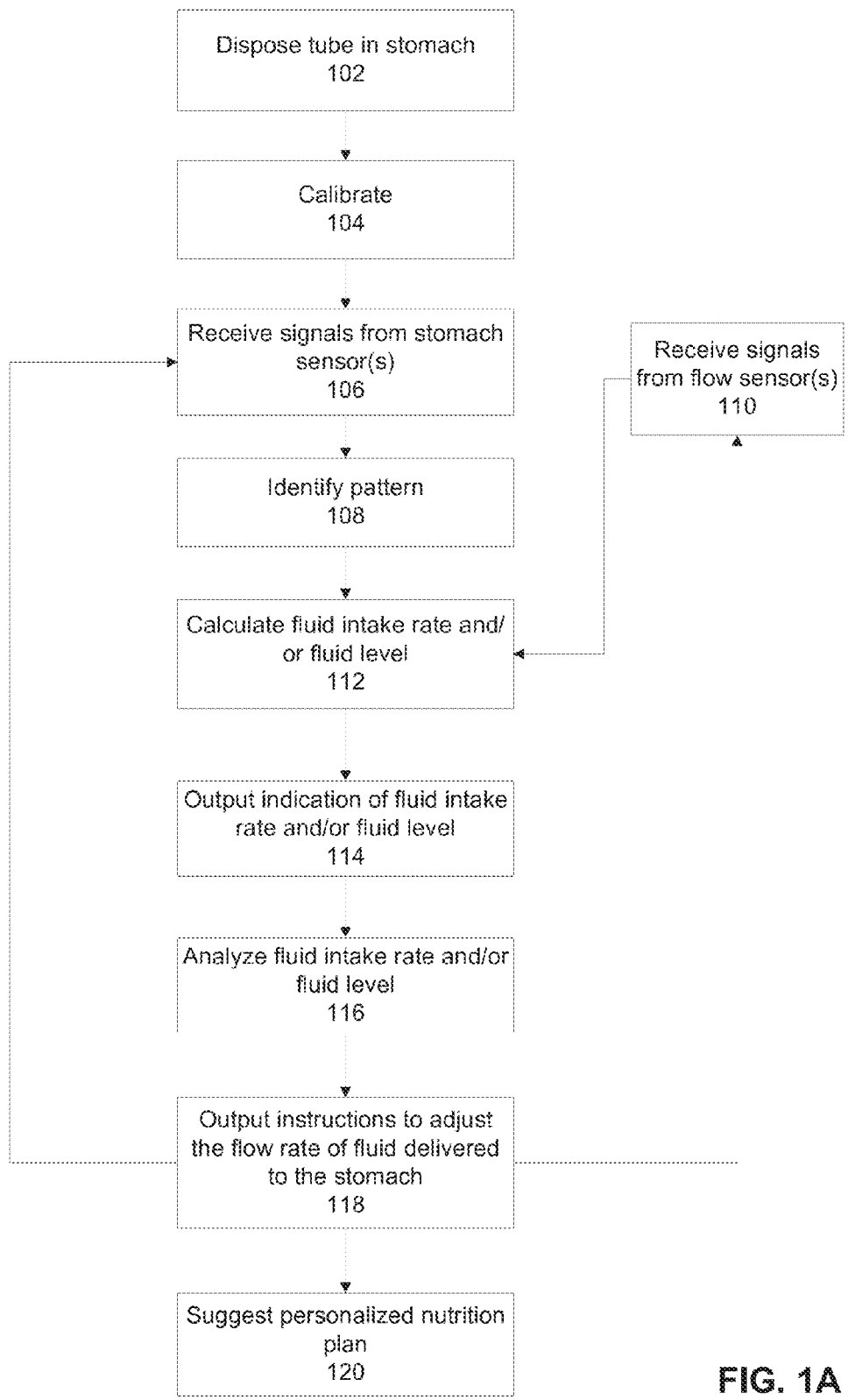
Figure 2:
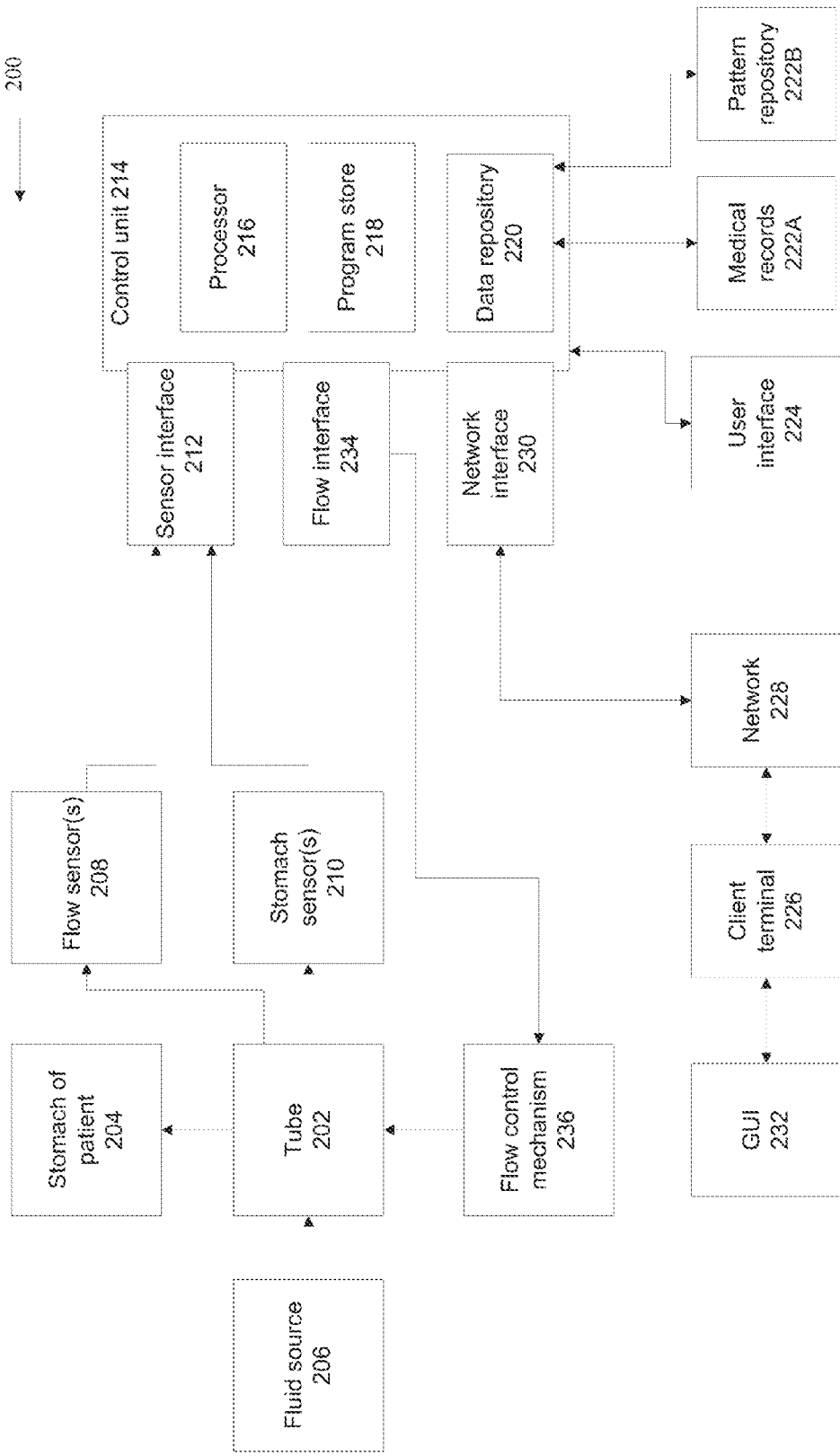

Reference is now made to FIG. 1A, which is a method for calculating a gastric emptying rate based on signals received from stomach sensors positioned in a stomach lumen of a patient, in accordance with some embodiments of the present invention. Reference is also made to FIG. 2, which is a block diagram of components of a system that calculates the gastric emptying rate based on signals received from stomach sensors positioned in the stomach of the patient, in accordance with some embodiments of the present invention. The flow rate of fluid being delivered to the stomach of the patient may be adjusted according to the calculated gastric emptying rate, optionally to maintain the fluid level of stomach fluid below a predefined requirement, which may reduce the risk of aspiration pneumonia. The adjustment may be performed to match the flow rate of fluid being delivered to the stomach of the patient to the actual ability of the patient to receive (e.g., ingest and/or absorb) the fluid, as measured by the calculated gastric emptying rate.

The systems and/or methods described herein provide a monitoring and/or control mechanism for a process that delivers fluids to a stomach of a patient using a tube. The systems and/or methods provide acts and/or functions that act in concert to improve the technical field of controlling and/or adjusting fluid delivery to the patient using the tube—closed loop feeding. By measuring (e.g., in real-time, or close to real-time) how the stomach of the patient is actually emptying, the systems and/or methods allow for dynamic control of the fluid delivered to the patient. Such control may help prevent complications, such as aspiration pneumonia, due to over feeding and filing of the stomach with an excess volume of fluid. Such control may help patients receive their requirement daily nutrients, by dynamically matching the fluid delivered to the patient with the ability of the stomach to empty the fluid contents into the small intestine, which may vary during the day, due to administration of medications, and/or due to other events.

The systems and/or methods described herein operate in a closed loop manner. A fluid delivery rate is selected for feeding the patient using the tube, for example, automatically generated based on patient parameters entered using a GUI. The gastric emptying rate which represents the real-time ability of the patient to safety ingest the food (i.e., reducing risk of aspiration pneumonia) is automatically calculated as described herein. The fluid delivery rate may be adjusted according to the gastric emptying rate, optionally matched to the gastric emptying rate. Suggestions for feeding may be automatically generated and presented on a GUI for selection by a user.

System 200 includes a tube 202 (optionally flexible) for insertion into a stomach of a patient 204. Tube is connected to a fluid source 206 (e.g., feeding bag) located externally to the body the patient, for example, a bag of nutrients for enteral delivery. One or more flow sensors 208 generate signals used to measure the flow rate of fluid from fluid source 206 being delivered to stomach of patient 204 via tube 202.

One or more stomach sensors 210 may be coupled to tube 202 (e.g., integrated within walls of tube 202, and/or temporarily affixed to tube 202, and/or permanently connected to tube 202) and/or inserted using another probe (e.g., solid or hollow tube). Signals generated by sensors 208 and/or 210 are received by a sensor interface 212 of control unit 214. One or more processors 216 (e.g., central processing unit, graphics processing unit, field programmable gate array, which may be organized as a cluster of processors for distributed processing) implement code stored in a program store 218 (e.g., a local and/or remote storage device and/or memory) to process the received signals, and calculate the gastric emptying rate and/or other values.

Control unit 214 may include or be in communication with a data repository 220 storing medical records 222A, and/or a pattern repository 222B (e.g., a database of patterns, a model of patterns, a trained statistical classifier for analyzing signals, and/or functions that map signals to one or more patterns.) Control unit 214 may be in communication with a user interface 224 that displays data and/or received data entered by a user, for example, a display, a touchscreen, a keyboard, a mouse, and voice recognition software.

Control unit 214 may be implemented in hardware and/or software, as a stand-alone unit, and/or integrated into an existing unit. For example, control unit 214 may be implemented by a server, as a unit integrated with flow control mechanism 236, or as a portable device.

Control unit 214 may communicate with one or more client terminals 226 over a network 228 (e.g., the internet, a private local network, a wireless network, a cellular network) via a network interface 230. Examples of client terminals 226 include tablets, laptops, mobile devices, smartphones, wearable computers, desktop computers, watch computers, and glasses computers. Code to implement a GUI 232 may be stored on client terminal 226.

Control unit 214 may communication using a flow interface 234 with a flow control mechanism 236 that automatically controls the flow rate of fluid through tube 202, for example, using a computer controlled pump and/or valve. Control unit 214 may generate instructions to dynamically adapt the flow rate by flow control mechanism 236.

The acts of the method described with reference to FIG. 1A, may be performed by system 200 described with reference to FIG. 2. Processing of signals, calculation of values such as the gastric emptying rate, and/or generation of instructions may be performed by processor(s) 216 of control unit 214 implementing instruction code stored in program store 218.

Optionally, at 102, tube 202 is positioned within stomach of patient 204, for example, threaded through the nose, the mouse, or a surgically created opening. Tube 202 may be coupled to stomach sensors 210, optionally coupled on a feeding tube. Alternatively, stomach sensors 210 are inserted separately from tube 202, for example, as a separate probe. Alternatively, stomach sensors 210 are inserted together with tube 202, for example, sensors 210 are located on a sheath positioned externally to tube 202, and inserted together with tube 202.

Stomach sensors 210 may be positioned along the length of the medial to the distal end portion of tube 202, spaced apart from one another. The spacing may be selected, for example, based on the desired precision in measurements (the number of sensors may be limited by the number of conductors that can be housed in the tube's wall). Closer spacing may allow for increased precision of measurements.

Stomach sensors 210 may include one or more different types of sensors.

Optionally, stomach sensors 210 include impedance sensors that measure impedance. Stomach sensors 210 generate electrical signals that may be processed to calculate impedance measurements.

Optionally, each impedance sensor includes one or more electrodes that may encircle tube 202. Optionally, each impedance sensor includes one or more annular or helical electrodes. Optionally, each impedance sensor includes parallel strip electrodes which are circular and dividedly placed around a common segment of the tube. Optionally, each electrode covers an area of about 1 square millimeters (mm2) and 150 mm2 or other values. Optionally, between 2 and 20 electrodes are used in each impedance sensor. Optionally, the distance between each pair of parallel electrodes is between about 3 mm and about 30 mm Optionally, the electrode is made of steel, stainless steel, brass, copper, platinum, silver, gold, aluminum alloy, zinc, nickel, tin, magnesium alloy, bronze, carbon of all sorts, phosphor bronze, conductive polymers and/or any composition thereof and/or any alloy therefrom. Optionally, the electrodes are printed on the peripheral surface of the tube. Optionally, the electrodes are coated with Gold, Silver, Nickel, Zinc, Tin, Copper and/or any composition thereof and/or any alloy therefrom. Optionally the conductive strip is later coated by an insulator such as parylane, the electrodes are shaped as circular, rectangular, and/or triangular spots. Additional details of exemplary impedance sensors are described, for example, with reference to United States Patent Application Publication Number 2013/0158514, incorporated herein in its entirety.

Alternatively or additionally, stomach sensors 210 include fluid sensors that measure the presence of fluid in proximity to the respective sensor. Fluid sensors may sense fluid, for example, by measuring pressure, using an ultrasound sensor, a laser sensor, and/or a dielectric sensor.

Alternatively or additionally, stomach sensors 210 include peristaltic sensors that detect stomach movement, such as contraction of muscles of the stomach. Examples of stomach sensors include pressure sensors that detect change in pressure due to stomach movement, and/or electrical and/or motion/strain sensors that detect electrical activity of moving muscles optionally an impedance sensor.

As used herein, the term tube may sometimes mean the feeding tube that delivers the fluid to the stomach of the patient, and/or may sometimes mean or include the tube portion connecting a feeding bag to the feeding tube, for example, when the feeding bag is sold separately from the feeding tube, and the feeding bag includes a tube component that connects to the feeding tube.

Figure 3:
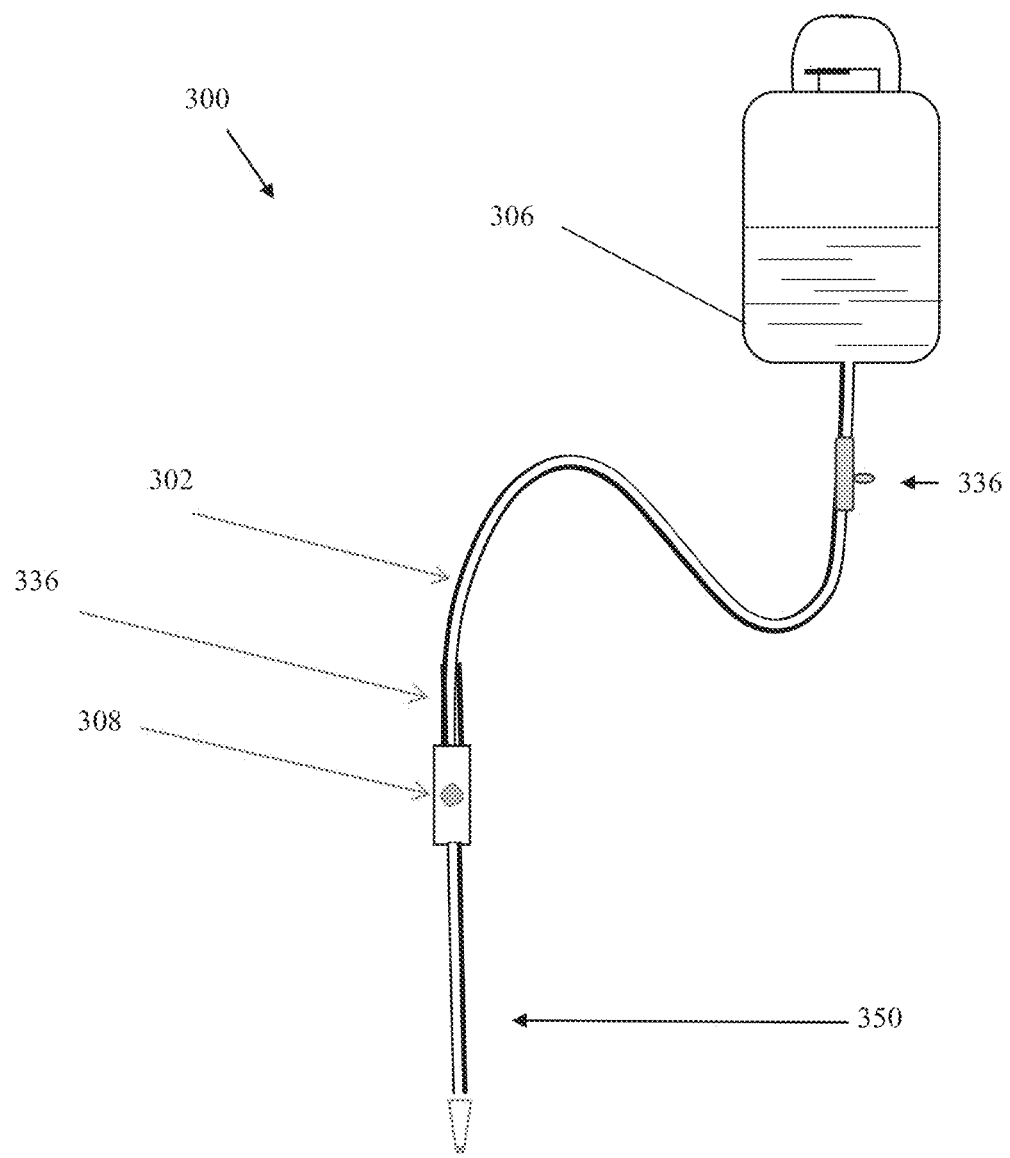

Reference is now made to FIG. 3, which is a schematic of an exemplary tube system 300 including one or more of: a connecting tube 302 (e.g., which connects to tube 202 of FIG. 2) for delivery of fluid (i.e., nutrition, food, water, medication) from a bag 306 (e.g., corresponding to reservoir 206) to the stomach of the patient, flow sensor(s) 308 (e.g., corresponding to flow sensors 208) for measuring the rate and/or volume of delivered fluid, and/or a flow control mechanism 336 (e.g., corresponding to flow control mechanism 236) for controlling the rate and/or volume of delivered fluid, in accordance with some embodiments of the present invention. System 300 may be designed for compatibility with existing feeding tubes, for example, having a connector section 350 designed for connecting to the enteral feeding tube that is inserted into the stomach of the patient.

Flow control mechanism 336 may be implemented, for example, as a pinch valve, a pump, and/or other flow control mechanisms that works in conjunction with 308 flow rate sensor, in a feedback mechanism to measure the flow rate and control the flow rate (e.g., according to the selected feeding rate). The pinch valve implementation allows different flexible (e.g., elastic) tubes 302 (which may be off-the-shelf) to be placed within mechanism 336, which controls flow by changing the cross sectional area of tube 302 by pinching the external walls. Mechanism 336 may be used with multiple disposable tubes 302.

An example of an implementation of flow sensor 308 is OEM Liquid Flow Sensors LG16/LG216 made by Senserion AG of Switzerland. Flow sensor 308 may be coupled to tube 302, for example, by a ring or semi-ring through which tube 302 passes. Optionally, flow sensor 308 is designed to measure the flow rate with an accuracy of about +/−1%, or about +/−5%, or about +/−0.5%, or other values. Optionally, flow sensor 308 is a drop and/or drip measurement and/or analyzer, for example, as described in International Patent Application No. IL2015/051143, filed on Nov. 24, 2015, by the same inventors as the present application, incorporated herein by reference in its entirety.

Tube 302 and/or bag 306 may be made from FDA approved polymer, or other materials approved for enteral feeding of patients.

Figure 4:
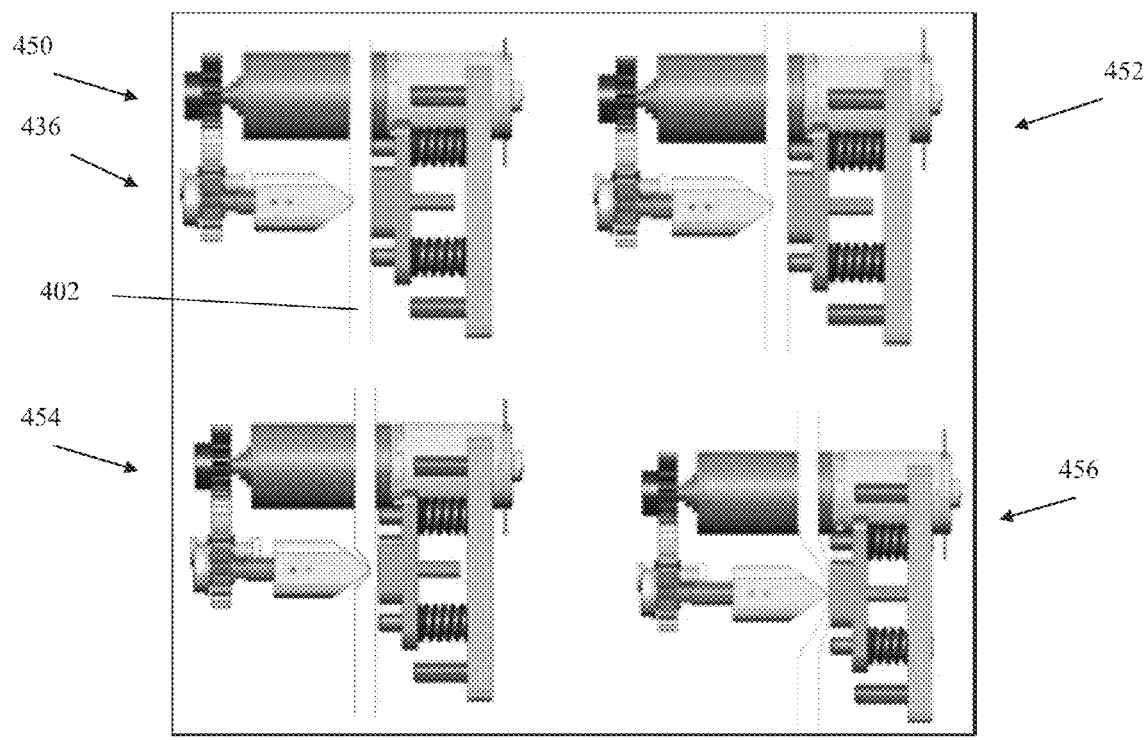

Reference is now made to FIG. 4, which is a schematic of an exemplary pinch valve 436 implementation of fluid control mechanism 236 and/or 336 for controlling the rate of fluid flowing through a tube into the stomach of a patient, in accordance with some embodiments of the present invention. Pinch valve mechanism 436 may be implemented, for example, based on a linear motor actuated pinch valve, and/or a motor driven eccentric pinch mechanism. Pinch valve mechanism 436 pinches tube 202 by applying pressure through the outer wall of tube to reduce the cross sectional area, reducing the rate of fluid flow. At 450, pinch valve 436 does not apply pressure to tube 402, allowing fluid flow through the complete cross sectional area. At 452 and 454, mechanism 436 applies partial pressure to reduce the cross sectional area of tube 202, reducing the rate of fluid flowing through tube 202. At 456, mechanism 436 applies full pressure to close off the cross sectional area of tube 202, preventing flow of fluid through tube 202.

Referring now back to FIG. 1A, optionally, at 104, a calibration is performed manually and/or automatically. The calibration may be performed by designating a baseline indicative of a value of a baseline stomach fluid volume and/or fluid level. The baseline may be used as a relative point and/or an absolute level from which increases or decreases in stomach fluid level and/or volume may be measured. The baseline stomach fluid level and/or volume may be measured automatically, for example, by detecting a pattern from stomach sensors 210, such as by pressing a calibration button to capture the initial baseline pattern (which may be stored in data repository 220). The level of fluid may be determined based on differences in signals generated by the stomach sensors. Sensors within the fluid may generate one type of signal, and sensors above the fluid may generate a different type of signal, allowing measurement or setting of the baseline of the actual location of the fluid level relative to the sensor position along the tube or probe. Optionally, the baseline is measured and/or set when the stomach of the patient is empty (i.e., of food, the stomach may include stomach secretions), for example, after the patient has not been fed for at least 6 hours, or 12 hours, or 24 hours, for example, as may occur upon admission of the patient, and/or in preparation for surgery.

Alternatively or additionally, the baseline may be measured, for example, by extracting the current fluid within the stomach (e.g., using a syringe or pump), measuring the extracted fluid volume, and setting the baseline according to the measurement. The extracted fluid may be returned to the stomach of the patient.

Optionally, a baseline gastric emptying rate is set, for example, by measuring a baseline change in stomach fluid level and/or volume over a predefined period of time, for example, an hour, or four hours. The baseline gastric emptying rate may be an absolute measurement, and/or a relative measurement from which changes in gastric emptying rate may be measured.

At 106, electrical signals from stomach sensors 210 are received by control unit 214 via sensor interface 212. Signals may be received by a wire and/or wireless communication channel. Signals may undergo processing before and/or after reception, for example, filtration, amplification, and/or analogue to digital conversion.

Signals may be received continuously, periodically, and/or other points in time.

At 108, the received electrical signals are analyzed to identify one or more patterns indicative of gastric emptying rate from the stomach lumen to a small intestine of the patient. The pattern indicative of gastric emptying rate may represent a fluid level or change in fluid level associated with the gastric emptying rate. For example, a rising fluid level may be indicative of a relatively lower gastric emptying rate, which may suggest a digestive problem due to delayed emptying. For example, a falling fluid level may be indicative of a relatively higher gastric emptying rate, which may suggest normal functioning of the digestive system. For example, a stable fluid level may be indicative of a shut down digestive system, or a steady-state in which the rate of fluid entering the stomach is substantially matched to the gastric emptying rate.

The analysis may be performed for individual spans of time (e.g., points in time or other short time periods) and/or based on multiple points in time and/or a continuous block of time, such as a time range and/or in loops every t time cycle.

The received electrical signals may be analyzed according to which sensor generated the respective signal, such as the position of the sensor along the tube associated with respective signal(s). The received electrical signals may be analyzed according to the sensor type that generated the signal.

The identification of the pattern may be performed based on data stored in pattern repository 222B, for example, by using a look-up table of experimental data measured from patients that maps sensor signals to empirically measured gastric emptying rates and/or empirically measured fluid volumes, by using a set of functions that calculated the gastric emptying rate and/or fluid level from the received signals, and/or a trained statistical classifier that classifies received signals into one of multiple gastric emptying rates and/or fluid levels. The pattern may be identified by matching the received signals to one or more stored patterns, optionally stored in a pattern database.

The identification of the pattern may be performed based on the impedance sensors measuring impedance. The impedance measurements may be used to identify the height of the fluid along the tube based on the sensor signals, based on impedance of air and fluid.

The identification of the pattern may be performed based on the fluid level sensors that detect the presence of fluid. The presence of air of fluid may be used to identify the height of the fluid along the tube based on the sensor where fluid switches to air.

The identification of the pattern may be performed based on the peristalsis (or other stomach mechanical and/or electrical activity) measured by the peristalsis sensors. The presence of one or more signal patterns of electrical and/or mechanical activity may be indicative of post-meal or intra-meal peristalsis.

Figure 5:
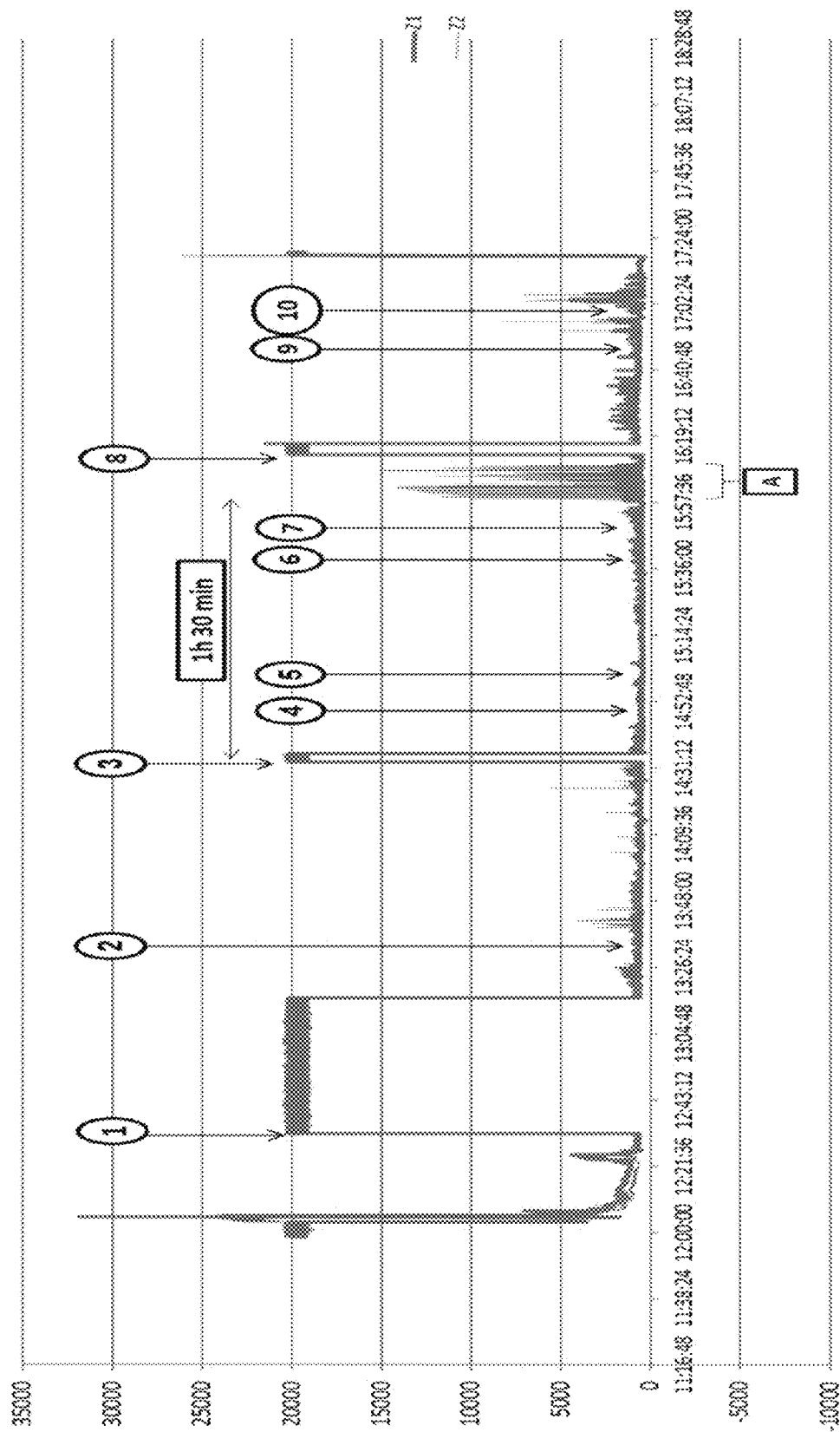
Figure 6:
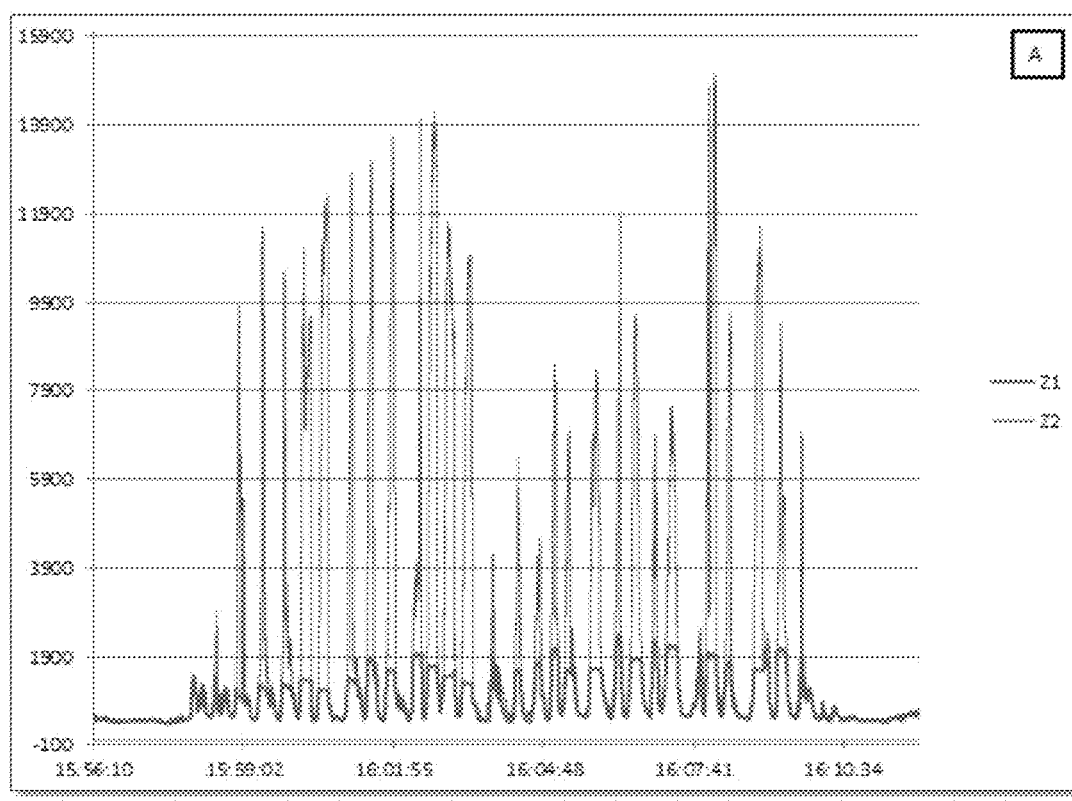

Reference is now made to FIG. 5, which is an exemplary recording of stomach activity recorded over several hours, in accordance with some embodiments of the present invention. The recording is based on impedance measurements from stomach sensors. The recording may be analyzed to identify one or more patterns indicative of peristalsis, and/or other patterns associated with food intake, and/or patterns indicating that the stomach is ready for another meal. The analysis may be performed by correlating the recording to delivered meals and/or measurements of gastric emptying. The identified patterns may be stored in pattern repository 222B, and used for matching sensor signals to detect significant stomach activity, which may be used to adjust fluid flow into the stomach of the patient. For example, FIG. 6 is a pattern identified from the recording of FIG. 5 representing peristalsis of the stomach after a meal, in accordance with some embodiments of the present invention. Matching sensor signals to the pattern of FIG. 6 indicates that the stomach is emptying its fluid contents, which may be a detected stomach emptying event. Based on the matched pattern, additional fluid may be delivered to the stomach based on the assumption that the stomach is ready for another feeding session. Other example of a pattern that may be matched includes detecting a rising impedance level, suggesting that air is present in the stomach, and that the stomach has additional space for food. Yet another example of a pattern that may be matched includes detecting the level of fluid reaching to the top of the stomach, such as by the stomach sensor close to the lower esophageal sphincter (LES), which indicates that the stomach is full (or at capacity, or close to full) of fluid, which may be used to generate instructions to stop fluid delivery.

Referring now back to FIG. 1A, optionally, the pattern is indicative of a volume and/or level of fluid in the stomach. The gastric emptying rate may be calculated based on detecting changes in the fluid volume and/or level in the stomach lumen over a period of time.

The pattern may be indicative of a relatively high fluid level in the stomach, for example, above a requirement (e.g., threshold or range), for example, above about 100 mL, or 150 mL, or 300 mL, or 500 mL, or other volumes. The high fluid level may represent a high risk for developing aspiration pneumonia.

The pattern may be indicative of a relatively low fluid level in the stomach, for example, below the requirement. The low fluid level may represent a low risk for developing aspiration pneumonia.

Figure 7:
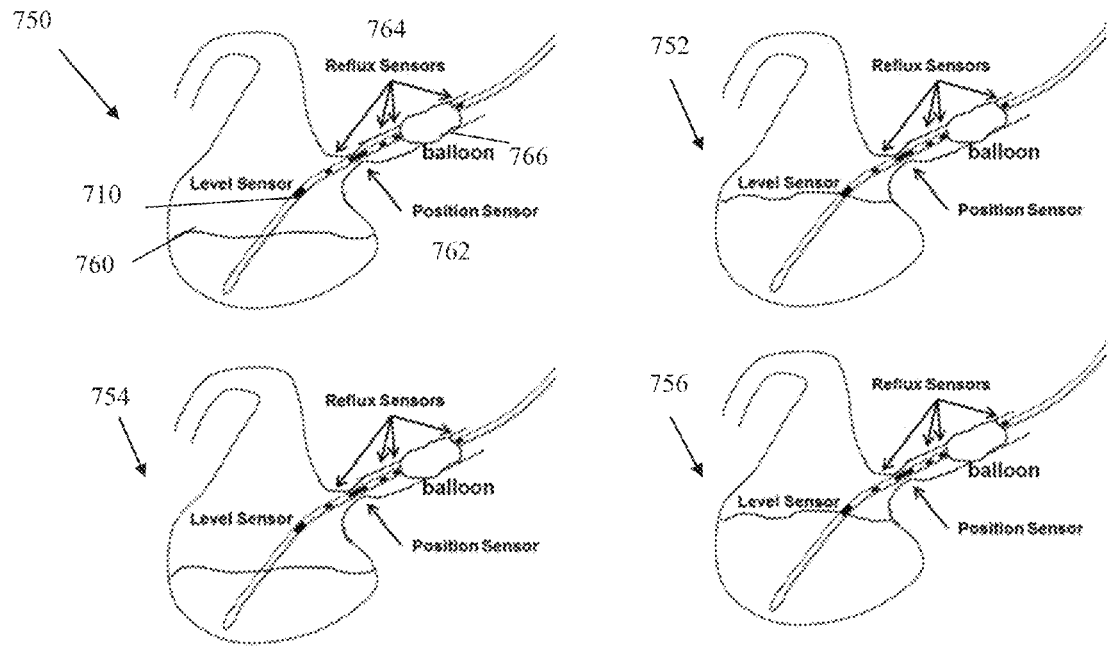

Reference is now made to FIG. 7, which is a schematic depicting a pattern based on fluid level in the stomach, and/or changes in the fluid level, in accordance with some embodiments of the present invention. Arrow 750 depicts a fluid level 760 which is below a level sensor 710 (e.g., fluid sensor, stomach sensor 210), which does not detect the presence of fluid, and/or detects the presence of air the stomach may be empty due to the fact that for a previous IV feeding. The detection of gastric content presence in sensor 710 in the upper stomach area, using impedance sensor for example, generates instructions to automatically stop the feeding process 752. Arrow 752 depicts a rise in the fluid level to reach the level sensor by filling the stomach using the tube or other means in a known pre-set flow rate, which detects the presence of fluid. The sensor detection may be indicative of, for example, a substantially full stomach after meal delivery, which may be used to generate instructions to automatically stop delivery of the fluid, for example for a pre-set by the system, "t" time, for example 60 minutes. Arrow 754 depicts a emptying of the stomach of the fluid level below the fluid sensor for the pre-set time, optionally below the level of 750. The pattern may be indicative of, for example, emptying of the stomach after and/or during a meal, which may be used to generate instructions to deliver more fluid and/or to calculate gastric emptying rate. Arrow 756 depicts a rise in the fluid level back to the level sensor with the same pre-set flow rate used in 752. The re-detection of fluids by the level sensor may be indicative of, for example, a rise in the fluid level of the stomach, and allow for example, the calculation of the gastric emptying rate in that exact point in time. Due to dynamic changes in patient condition in ICU 750-756 process may be automatically repeated every "z" time which may indicate on improvement or declining patient state. Instructions may be automatically generated to stop or reduce the rate of fluid delivery. The gastric emptying rate representing the gastric emptying rate may be calculated, for example based on the relationship Quantity=Digestion Rate×(Interval Time+Feeding Time).

Referring now back to FIG. 1A, the pattern may be indicative of emptying of the stomach of an enterally delivered food dose, that the stomach empty and in a state ready for a next enterally delivered food dose, a delayed emptying of the stomach of the enterally delivered food, and that the stomach is filling up with enterally delivered food.

Optionally, at 110, flow rate signals are receive by control unit 214 from flow sensor(s) 208 via flow interface 234. Signals may be received by a wire and/or wireless communication channel. Signals may undergo processing before and/or after reception, for example, filtration, amplification, and/or analogue to digital conversion.

Signals are processed to obtain measurements of the volume and/or rate of flow of fluid delivered to the stomach of the patient. The measurements may be calculated by control unit 214 and/or flow control mechanism 236, and/or by flow sensor 208.

At 112, the gastric emptying rate is calculated based on the identified pattern, optionally in view of the received flow rate measurement. Alternatively or additionally, a stomach emptying event is detected based on the identified pattern, for example, by detecting a stomach peristalsis event and/or detecting a decrease in the fluid level, and/or detecting a stable fluid level in view of a flow rate of fluid entering the stomach. The calculation may be performed by processor 216 of control unit 214 implementing code stored in program store 218.

Optionally, the fluid level in the stomach is calculated manually and in 4 hours intervals (as indicated in the literature), based on the identified pattern. The fluid level in the stomach may be indicative of the gastric residual volume (GRV), and may be used by healthcare professionals to make medical decisions based on GRV. The GRV may be indicative of the risk of developing aspiration pneumonia, and/or used in making feeding decisions. The gastric emptying rate may be calculated based on the calculated fluid level. The down side of this method is that it is manual labor for the nurses (approx. 5 minutes to each patient) every 4 hours and to all patients in the unit-30 minutes per patient per day. Yet another problem is the food wasted in the GRV-suction method, repeatedly. But the biggest downside is that it is not real-time. The patient may have reflux in between the 4 hours (which they do) and that causes aspiration of gastric fluid to the bronchial tree and lungs that causes pneumonia.

The gastric emptying rate may be calculated based on changes in the fluid level relative to the baseline pattern, for example, whether the fluid level in the stomach is rising, falling, or staying the same over a predefined period of time.

The calculation of the gastric emptying rate may be based on the identified pattern of stomach peristalsis (or other electro-mechanical stomach activity). For example, guiding the calculation on whether the stomach appears to be emptying, or at rest.

Exemplary methods for calculating the gastric emptying rate include:

When the identified pattern is indicative of emptying of the stomach of an enterally delivered food dose, the gastric emptying rate may be calculated as approximately equal to the flow rate of fluid entering the stomach, based on the assumption that the stomach is able to empty the entering fluid. When the stomach contains fluid, the gastric emptying rate may be calculated as the flow rate of fluid entering the stomach added to the fluid inside the stomach, based on the assumption that the stomach is able to empty both the entering fluid and the current stomach contents.

When the identified pattern is indicative of that the stomach is empty and in a state ready for a next enterally delivered food dose, the gastric emptying rate may be calculated as zero, based on the assumption that the stomach is ready to accept more fluid but fluid is not currently being delivered.

When the identified pattern is indicative of a delayed emptying of the stomach of the enterally delivered food, the gastric emptying rate may be calculated as the difference between the flow rate of fluid entering the stomach and the rising fluid volume in the stomach, based on the assumption that the stomach is not emptying the entering fluid fast enough.

When the identified pattern is indicative of that the stomach is filling up with enterally delivered food, the gastric emptying rate may be calculated as the difference between the flow rate of fluid entering the stomach and the rising fluid volume in the stomach, based on the assumption that the stomach is not emptying the entering fluid fast enough.

When the identified pattern is indicative of a rising fluid level, the gastric emptying rate may be calculated as the difference between the flow rate of fluid entering the stomach and the rate of rise of the fluid volume in the stomach, based on the assumption that the stomach is not emptying the entering fluid fast enough.

When the identified pattern is indicative of a falling fluid level, the gastric emptying rate may be calculated as the sum of the flow rate of fluid entering the stomach and the fluid volume in the stomach that is decreasing, based on the assumption that the stomach is emptying both the fluid entering the stomach and the current volume of fluid in the stomach.

When the identified pattern is indicative of a substantially stable fluid level (e.g., according to a predefined requirement), the gastric emptying rate may be calculated as approximately equal to the flow rate of fluid entering the stomach, based on the assumption that the fluid entering the stomach is being emptied by the stomach.

When the identified pattern is indicative of a high fluid level (e.g., above the requirement and/or within a range) the GRV may be calculated, for example, by calculating the absolute value of the volume currently in the stomach, and/or based on the flow rate of the fluid that entered the stomach less the calculated gastric emptying rate that exited the stomach. The GRV may be used to assess the risk of aspiration pneumonia, and optionally to lower the flow rate of fluid entering the stomach to reduce the risk.

When the identified pattern is indicative of a low fluid level (e.g., below the requirement and/or within a range), the GRV may be calculated and/or monitored, and/or the flow rate of fluid entering the stomach may be monitored, for example, to ensure that the total nutrient requirements of the patient are being met with sufficient fluid flow into the stomach of the patient.

When the identified pattern is indicative of a desired fluid level (e.g., within a range), the GRV may be calculated and/or monitored, for example, to maintain the GRV at the desired fluid level.

At 114, an indication of the calculated gastric emptying rate, and/or calculated fluid level, and/or identified pattern, and/or identified stomach emptying event is outputted by control unit 214. The indication may be formatted for presentation and/or storage.

The indication may be transmitted for presentation by GUI 232 and/or user interface 224, for example, displayed as a number, message, and/or graph on a display. The indication may be stored in data repository 220, optionally for use in other calculations, to assess trends and/or calculate long term gastric emptying rates. The indication may be transmitted to other processes implemented by a processor executing code instructions, for example, to update the trained statistical classifier, and/or collect research data.

Optionally, at 116, the gastric emptying rate and/or fluid level is analyzed by control unit 214, by processor 216 implementing code stored in program store 218.

Optionally, the analysis includes comparing the calculated gastric emptying rate to a target fluid delivery rate. The target fluid delivery rate may represent the amount of fluid that the patient requires in order to be supplied with sufficient nutrients. The target fluid delivery rate may be obtained, for example, manually entered by a user, retrieved from a database, and/or calculated from an equation or algorithm.

The target fluid delivery rate may be variable (e.g., represented as a function of time, a function of meal events, and/or a function of medications), for example, varying throughout the day, according to when meals are administered, and/or according to when medications are administered. The comparison may be performed, for example, continuously, and/or iteratively such as at defined periods of time, for example, hourly.

The comparison process may generate an indication: when the target fluid delivery rate is being met, is predicted to be met, is not currently being met, is currently being met but predicted not to be met, or is currently not being met but predicted to be met.

Alternatively or additionally, the calculated gastric emptying rate is compared to the measured flow rate of fluid entering the stomach. The comparison process may generate an indication: when the gastric emptying rate matches the measured flow rate (i.e., within a tolerance requirement) which may indicate that fluid is being delivered correctly, when the gastric emptying rate is higher than the measured flow rate which may indicate that the patient is not being supplied with sufficient fluid, and when the gastric emptying rate is lower than the measured flow rate which may suggest that the patient is being overfed and at risk of aspiration pneumonia.

Alternatively or additionally, the volume and/or level of fluid in the stomach is monitored, by comparing the volume and/or fluid level to the gastric emptying to a target requirement (e.g., threshold, range), for example, defined based on risk of aspiration pneumonia. An indication of whether the volume of fluid in the stomach meets the requirement or does not meet the requirement may be generated and presented. The target requirement may vary, for example, as a function of time, meal administration, and/or drug delivery.

The comparison may be performed within a predefined margin of tolerance.

At 118, control unit 214 generates instructions to dynamically adjust the flow rate of fluid entering the stomach lumen from an external source according to the comparison. The instructions are designed to match the flow rate to the gastric emptying rate, for example, to increase or decrease the current flow rate according to the calculated gastric emptying rate. The instructions are outputted via flow interface 234 for implementation by flow control mechanism 236, optionally automatically and dynamically. In this manner, the flow rate is dynamically and automatically adjusted, optionally in real time, to help make sure that the patient is receiving adequate nutrition, while reducing the risk of aspiration pneumonia due to over feeding, and/or reducing the risk of malnutrition due to under feeding.

Instructions may be formatted, for example, as machine readable code, as a human readable script, as network messages, and/or in other formats.

At 120, the fluid treatment plan is automatically evaluated, optionally by control unit 214, and/or client terminal 226, and/or an external server.

Figure 8:
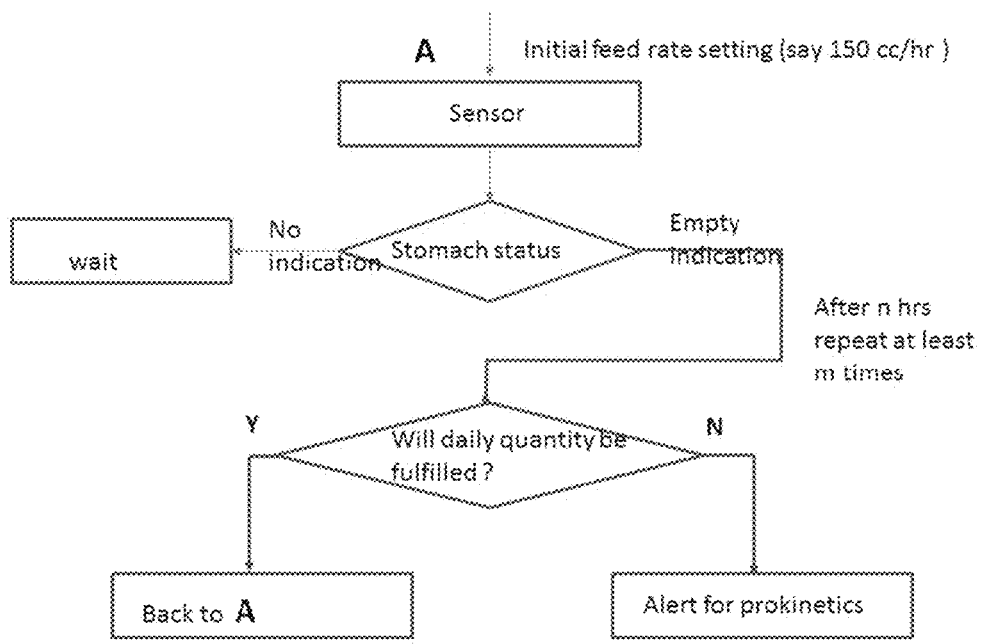

Optionally, an indication suggesting administration of a gastroprokinetic drug is generated when the gastric emptying rate is lower than the target fluid delivery rate according to a target gap. The indication may be generated when the flow rate of fluid entering the stomach is above the gastric emptying rate, and/or when the fluid level in the stomach is rising. Such a scenario may suggest that the gastrointestinal activity of the patient is suppressed and needs medical assistance in order to be able to receive the necessary nutrients. The indication may be displayed as a message to health professionals, for example, by GUI 232 and/or on use interface 224, and/or transmitted to an automatic drug delivery machine to automatically administer the drug. Reference is now made to FIG. 8, which is a flowchart of an exemplary method for generating an indication suggesting administration of the gastroprokinetic drug, in accordance with some embodiments of the present invention. The indication for gastroprokinetic is generated when the stomach is determined to be at a low fluid level state and/or the calculate gastric emptying rate is low, and the daily nutrient requirements are not being met, or predicted to not be met.

Referring now back to block 120 of FIG. 1A, alternatively or additionally, a suggested personalized nutrition regimen is created for the patient according to the indication of the gastric emptying rate, by control unit 214, by client terminal 226, and/or by another server. GUI 232 presents the suggested personalized nutrition regimen on a display of client terminal 226. Code calculates the suggested personalized nutrition regimen for the patient according to the indication of the gastric emptying rate and the medical state of the patient.

The suggested personalized nutrition regimen may be selected using a datastore storing at least one medical state of the patient affecting diet, such as medical records 222A, for example, whether the patient has kidney impairment, diabetes, cardiovascular disease, and/or other medical conditions that require special diets. The ability of the patient to absorb and/or ingest the food, which may be determined based on the calculated gastric emptying rate, may be used to determine the fluid delivery plan for the patient.

The fluid delivery plan may be automatically administered and/or monitored by the systems and/or methods described herein.

Figure 1B:
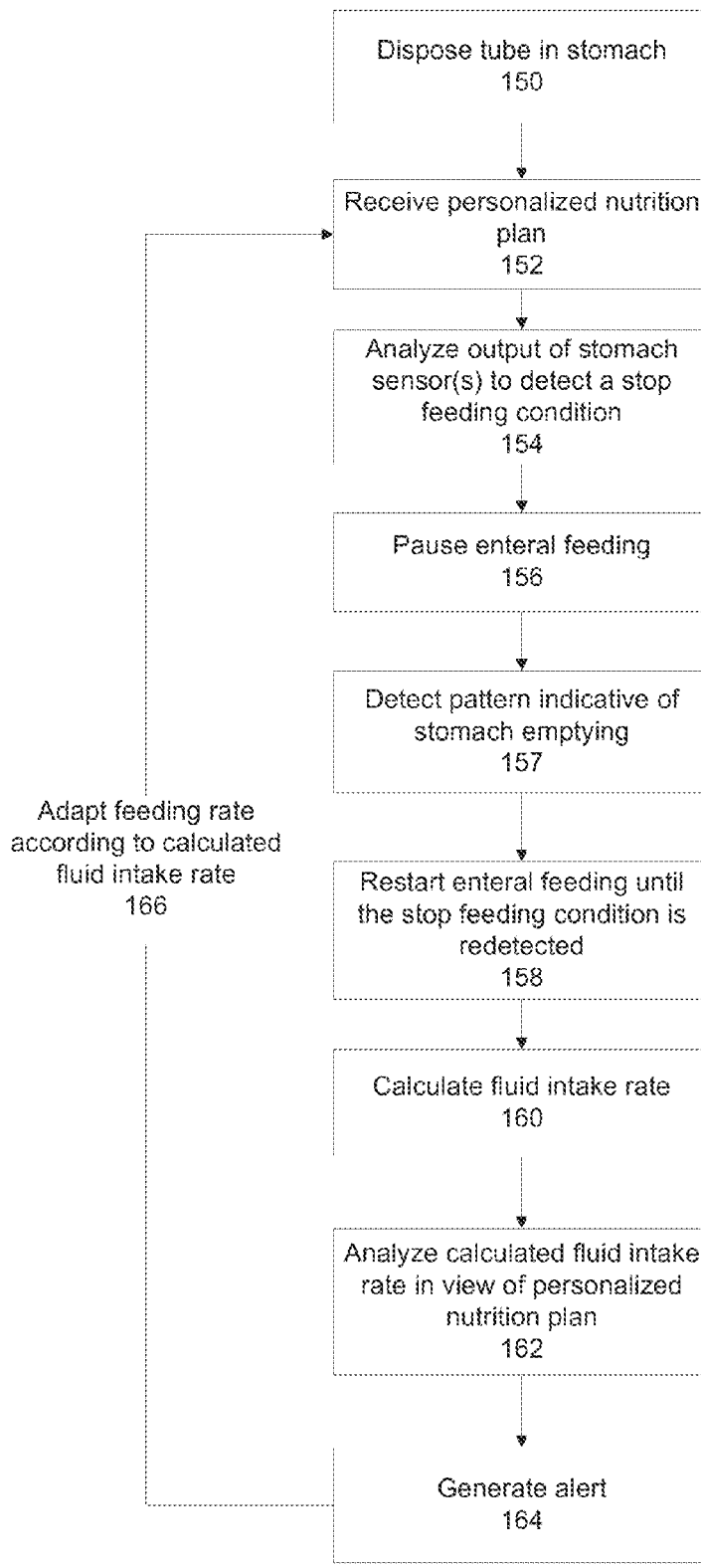

Reference is now made to FIG. 1B, which is a flowchart of another exemplary method for automatic calculation of the gastric emptying rate, in accordance with some embodiments of the present invention. The method of FIG. 1B may be implemented by system 200 of FIG. 2, for example, one or more acts of FIG. 1B are executed by processor 216 of control unit 214 implementing code stored in program store 218. The acts of the methods may be performed during an enteral tube feeding session (using the tube in the stomach of the patient) by a feeding mechanism (e.g., flow control mechanism 236 of FIG. 2). The method of FIG. 1B may be a variation of the method described with reference to FIG. 1A. Reference will also be made to FIG. 7 to illustrate the acts of the method.

At 150, a tube is disposed in the stomach, for example, as described with reference to block 102 of FIG. 1A.

Optionally, tube 202 includes one or more stomach sensors 210 located at a predefined distance away from the distal end of tube 202, and tube position is continuously monitored and in real time, optionally, using the systems and/or methods (e.g., sensors) described in International Patent Application No. IL2015/050262 filed on Mar. 12, 2015, incorporated herein by reference in its entirety, for the verification that the portion of the tube is in its supposed location, for example, about 5 centimeters (cm), or about 10 cm, or other distances. The location of sensor 202 may be selected to be within the stomach, in proximity to the lower esophageal sphincter (LES), but not within the esophagus, for example, within about 1 cm, or about 3 cm o the LES. The location of the stomach sensor 210 may be selected (e.g., by the manufacturer, which may fix the stomach sensor at the selected location on a tube being sold) based on the predicted size and/or volume of the stomach, such that the sensor is located within the fluid, close to the fluid-air interface when the stomach is full or mostly full with fluid. Optionally, a single sensor 210 is used. For example, sensor 710 as shown in image 750 of FIG. 7. The stomach may include a known or un-known amount of fluid, for example, shown as a first fluid level 760 in image 750 or can be completely empty.

At 152, a personalized nutrition plan for feeding of the patient using tube 202 is received by control unit 214, for example, as discussed with reference to block 120 of FIG. 1A. The personalized nutrition plan includes a target fluid delivery rate (e.g., mL/hour), which may vary, for example, at different hours of the day retrieved automatically by the dietician using an app on a tablet, laptop or smartphone using patient data inserted or automatically collected from electronic patient medical records, along with his personal restriction e.g. lactose intolerance, and his condition using disease base algorithm or harris benedict algorithm that are known in the literature—as shown in FIGS. 13A-13D.

The personalized nutrition plan may be automatically calculated for the patient based on one or more patient parameters, using tables, equations, relationships, and/or other methods of calculating personalized nutrition plans, for example, as discussed with reference to FIGS. 9-10.

Optionally, GUI 232, which may be implemented by executing instruction code by client terminal 226 or control unit 214 (e.g., via user interface 224), allows a healthcare worker to enter patient parameters and calculate the personalized nutrition plan.

Reference is now made to FIGS. 13A-13D, which are exemplary GUI screens for allowing a healthcare worker to enter patient parameters for automatic determination of the personalized nutrition plan, in accordance with some embodiments of the present invention.

Figure 13A:
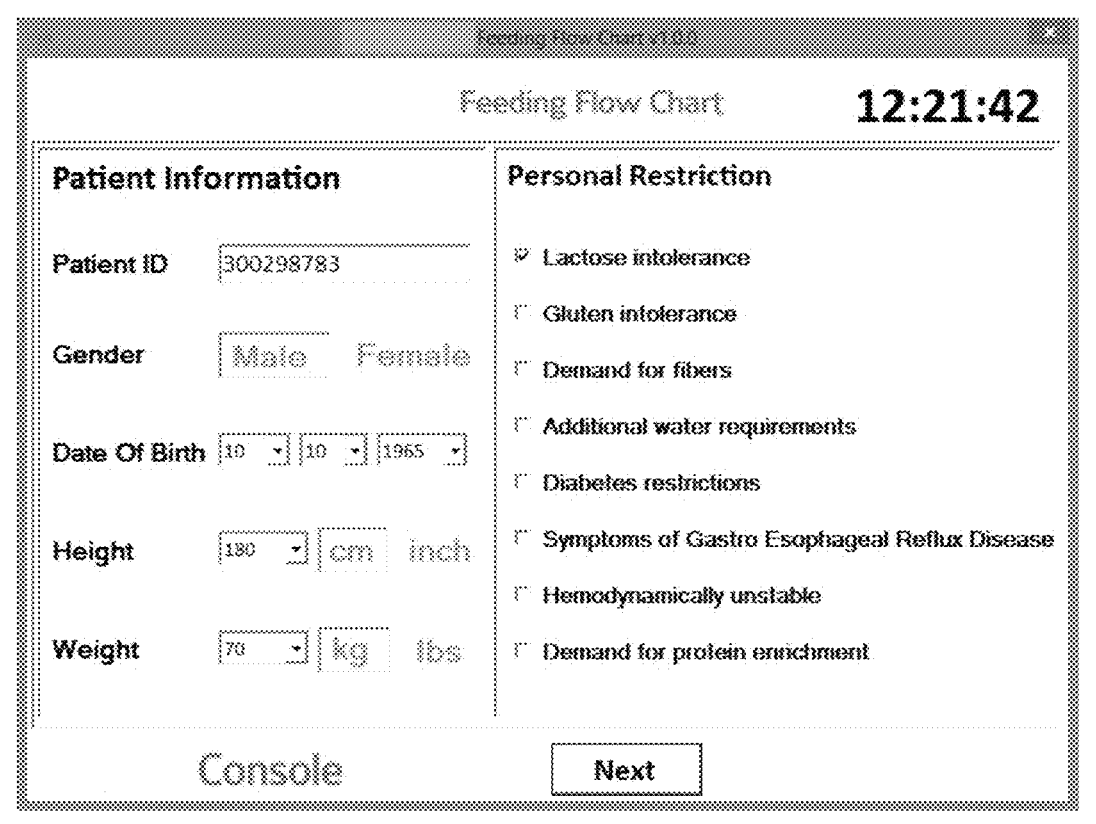

FIG. 13A is a GUI screen allowing the healthcare worker to enter patient data, such a demographics (e.g., gender, date of birth, height, weight), and medical restrictions on diet. GUI may allow the healthcare worker to enter a patient ID, which may link to electronic patient medical records.

Figure 13B:

FIG. 13B is another GUI screen, which may following the screen of FIG. 13A. The GUI of FIG. 13B may display a suggested meal plan, and/or allow the user to adjust the suggested plan. The GUI may allow the use to select the method of calculating the suggested plan, for example, based on Harris-Benedict equation, or based on disease condition. The GUI may display patient parameters calculated from the data entered using the GUI of FIG. 13A, for example, age and body mass index (BMI). The GUI may allow entering additional data, for example, medical conditions the patient is currently experiencing (e.g., acute conditions).

Figure 13C:
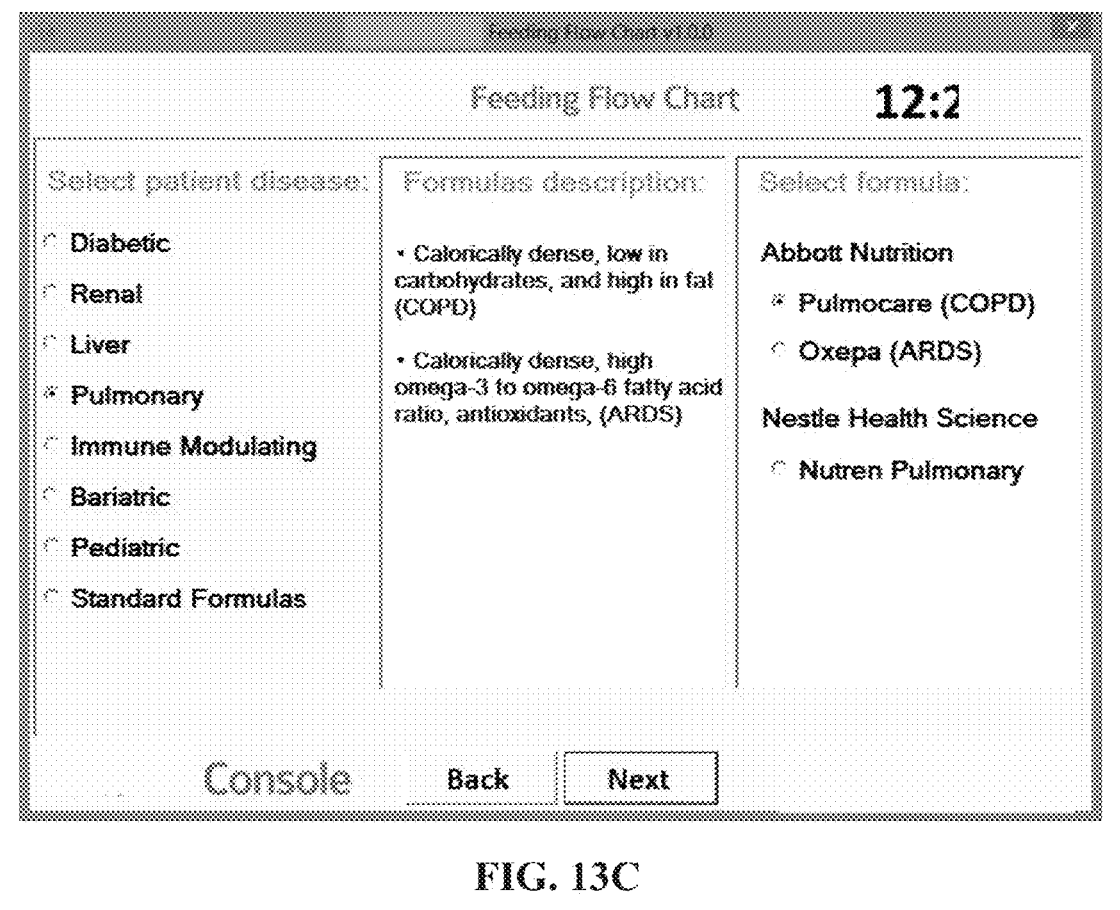

FIG. 13C is yet another GUI screen, which may following the screen of FIG. 13B. The GUI of FIG. 13C allows the user to select additional patient diseases (e.g., chronic conditions). The GUI may display different formulas that are available, from which the user may select.

Figure 13D:
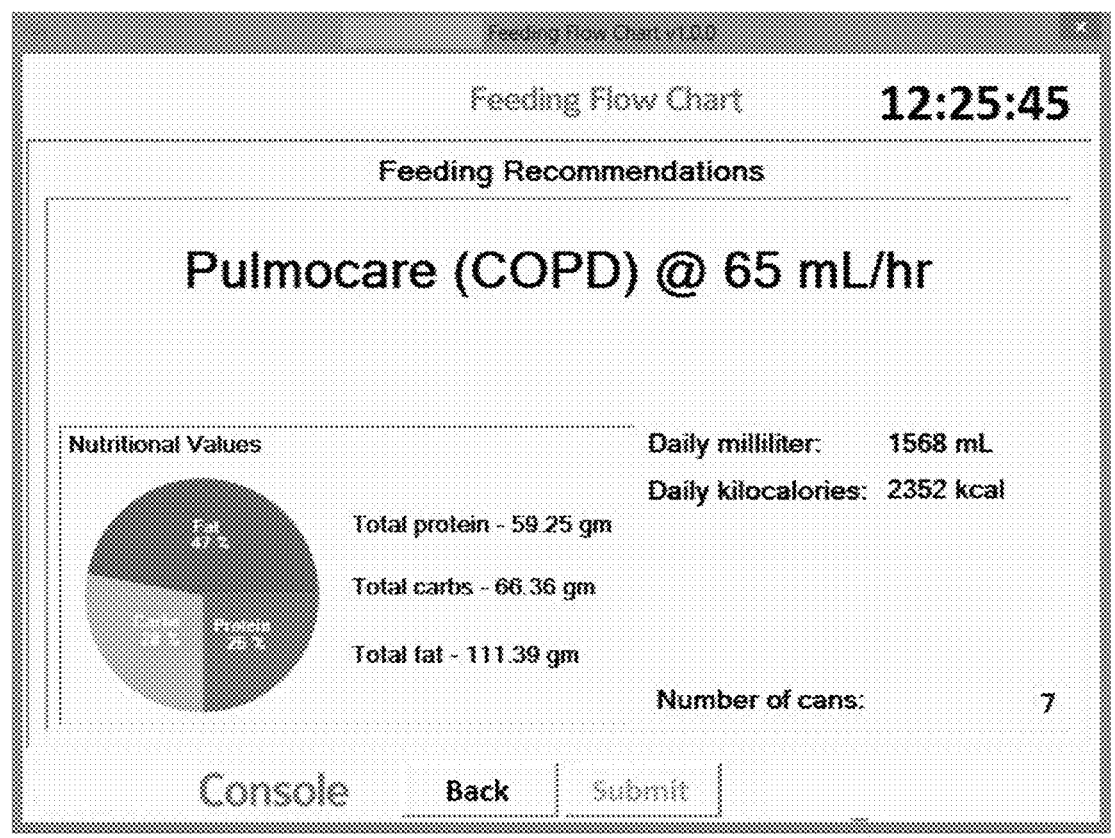

FIG. 13D is yet another GUI screen, which may follow the screen of FIG. 13C. The GUI of FIG. 13D displays the determined personalized nutrition plan for the patient, based on the patient data entered in earlier screens. For example, a fluid deliver rate of 65 mL/hour, to achieve a total daily delivered volume of 1568 mL this allows a dietician or head of ICU to submit remotely the nutrition plan and get real-time alerts on gastric emptying problem and flow rate and suggest action.

The patient may be fed (i.e., delivery of fluid via the tube) at the target fluid delivery rate based on the personalized nutrition plan, for example, using the flow control mechanism 236, as described herein.

Referring now back to FIG. 1B, at 154, outputs of one or more stomach sensors 210 are analyzed to detect a stop feeding condition. The stop feeding condition may be indicative of the stomach of the patient being full, or mostly full. The stop feeding condition may be selected to reduce risk of aspiration pneumonia in the patient, by selecting the maximum tolerable volume of fluid that the stomach may contain.

Optionally, a first amount of fluid volume is delivered to the stomach of the patient until the stop feeding condition is met. The delivery of fluid may be monitored, for example, by flow sensor(s) 208. The volume delivered until the stop feeding condition is met may be measured. The fluid volume may be automatically delivered to the patient via tube 202 as described herein, for example, using flow control mechanism 236, and measured using flow sensors 208 as described herein.

Optionally, the stop feeding condition is met when the fluid level of the fluid inside the stomach reaches the stomach sensor 210 located on the tube within the stomach, for example, as shown with reference to image 752 of FIG. 7, which depicts fluid level 760 reaching sensor 710.

The stop feeding condition may be detected when sensor 210 detects a change from air to fluid, indicating that the fluid level in the stomach rose to the level sensor 210 is located at.

The measured delivered fluid volume may be stored in a memory of control unit 214.

At 156, control unit 214 measures a predefined period of time.

Optionally, the enteral tube feeding is paused during the predefined period of time, for example, by generating instructions to halt flow of fluid by flow control mechanism 236. Optionally, no additional fluid volume is delivered during the period of time. Alternatively, the fluid volume delivered during the period of time is measured and added to update the second delivered fluid volume (described with reference to block 158).

The enteral tube feeding may be paused, and/or the predefined period of time may start, in response to the detected stop feeding condition being met.

The predefined period of time may be automatically determined, or manually entered by the user in advance, or marked by the user pressing a start/stop button on the control unit. The predefined period of time may be dynamically determined, for example, by measuring signals from stomach sensors and analyzing the signals to detect stomach peristalsis indicative of stomach emptying.

The predefined period of time may be selected to correspond to approximately the amount of time expected for the patient's stomach to empty itself of a fluid meal. The predefined period of time may be selected according to the next expected meal time of the patient.

The predefined period of time is, for example, about 1 hour, about 2 hours, about 4 hours, about 6 hours, or other periods of time.

Image 754 of FIG. 7 is an exemplary representation of the state of fluid level 760 at the end of the predefined period of time, located substantially lower than level sensor 710.

Optionally during the feeding session and/or during the pause, at 157, a pattern indicative of stomach emptying (i.e., fluid leaving the stomach for the intestines) is detected. The pattern may be indicative of peristalsis associated with stomach emptying. The pattern may be based on an analysis of stomach sensors that measure stomach activity, for example, electrical and/or mechanical activity of stomach muscles that correlate to a predefined pattern, which may be stored in a database (e.g., as shown and discussed with reference to FIGS. 5-6), for example, as described with reference to block 108 of FIG. 1A.

The detect pattern may be used to define the pause of the period of time of block 156, for example, the end of the period of time may be dynamically determined when the pattern of stomach emptying is detected, or when a set of peristalsis patterns indicating sufficient emptying of the stomach are detected.

Alternatively or additionally, block 157 may be performed during feeding of the patient, for example, delivery of the target fluid delivery rate as determined by the personalized nutrition plan. The personalized nutrition plan and/or the target fluid delivery rate may be adjusted (block 166) based on the detected stomach emptying events, for example, by comparing the identified stomach emptying events to expected stomach emptying events (which may be calculated using functions, obtained from a database, and/or manually entered). For example, when fewer stomach emptying events are detected than expected, the patient may be digesting slower, and the target fluid delivery rate may be reduced, and/or indications for administration of gastroprokinetics may be generated.

At 158, the enteral tube feeding is restarted after the predefined period of time, optionally by transmitting instructions to flow control mechanism 236. The patient is fed by delivery of fluid until the stop feeding condition is redetected by an analysis of outputs of stomach sensor(s) 210, for example, as described with reference to block 154. Optionally, a second amount of fluid volume is delivered to the stomach until the stop feeding condition (i.e., of block 154) is re-detected. The second amount of delivered fluid is measured. The delivery of fluid may be monitored, for example, by flow sensor(s) 208.

Image 756 of FIG. 7 depicts that fluid level 760 again reaches sensor 710.

At 160, the gastric emptying rate is calculated. The gastric emptying rate is calculated based on the amount of fluid (i.e., feeding content) delivered during the period between restarting of the feeding session and re-detection of the stop feeding condition (e.g., the measured second volume).

The volume of fluid emptied by the stomach during the predefined period of time is represented by the measured second fluid volume. The rate of fluid emptying by the stomach (i.e., gastric emptying rate) is calculated by dividing the second fluid volume by the period of time, to calculate the rate in terms of volume per unit of time (e.g., mL/hour).

The gastric emptying rate may be calculated or adjusted based on the detected stomach emptying patterns. The gastric emptying rate may be analyzed based on the detected stomach emptying pattern(s), for example, the gastric emptying rate may be correlated with the emptying patterns using a table of values, equations, and/or other methods. For example, one set of pattern may be correlated with a first emptying rate, and another second of pattern may be correlated with a different emptying rate.

At 162, the calculated gastric emptying rate is analyzed according to the received personalized nutrition plan (i.e., block 152). The calculated gastric emptying rate may be compared to the fluid delivery rate determined as part of the personalized nutrition plan, to determine whether the patient is able to empty stomach contents according to the plan (e.g., within a predefined tolerance range), is unable to empty stomach fluid contents according to the plan, or is able to empty more fluid than the patient is determined to receive according to the plan. Additional analysis details may be found, for example, with reference to block 116 of FIG. 1A.

At 164, an indication is generated indicating the calculate intake rate, optionally in comparison to the personalized nutrition plan, for example, as described with reference to block 118 of FIG. 1A. For example, an alert is transmitted to a mobile device of the healthcare work in the form of a message for presentation on the display of the mobile device.

Optionally, when the analysis determines that the gastric emptying rate is less than the rate of the personalized nutrition plan, a message indicating possible administration of gastroprokinetic medication is generated (and optionally transmitted) for presentation on the display (e.g., of the mobile device).

Optionally, at block 166, instructions are generated and/or transmitted to the feeding mechanism (e.g., flow control mechanism 236) to adapt the fluid delivery rate (i.e., feeding rate) of the enteral tube feeding according to the calculated gastric emptying rate. In this manner, the patient is fed at the rate at which the patient's stomach is actually able to empty itself into the intestines, which may help prevent or reduce the risk of aspiration pneumonia from overfeeding, and/or help prevent or reduce the risk of underfeeding the patient (e.g., due to a fear of overfeeding and aspiration pneumonia).

Optionally, the personalized nutrition plan is adjusted according to the calculated gastric emptying rate. The personalized nutrition plan may be dynamically adjusted to match the actual gastric emptying rate of the patient, represented by the calculated gastric emptying rate. Adjustments may be performed, for example, after every elapsed period of time (e.g., block 156), or shorter time intervals, or longer time intervals.

The adjustment may be automatic, optionally by control unit 214 creating instructions that are transmitted for implementation by flow control mechanism 236, for example, as described with reference to block 118.

Blocks 154-164 may be performed, optionally multiple times during feeding of the patient at the target fluid delivery rate, for example, at set intervals (e.g., every 4 hours, every 6 hours), and/or at events. Repeating blocks 154-164 may be used to measure the current patient intake rate, and to adjust the target fluid delivery rate accordingly.

The patient intake rate q (also referred to herein as gastric emptying rate) may be estimated according to the equation:

$$q=Q/(T-t)$$

Where Q denotes the volume of fluid needed to fill the stomach from sensor Z1 (low fluid level) to sensor Z2 (high fluid level).

T denotes the elapsed gastric emptying time from fluid level Z2 to Z1, and t denotes the filling make up time.

Alternatively, when fluid reaches Z2 feeding stops for a time period T then, feeding is resumed until level Z2 is reached and the required time t is measured.

The patient intake rate may be re-calculated according to the above mentioned equation.

Figure 9:
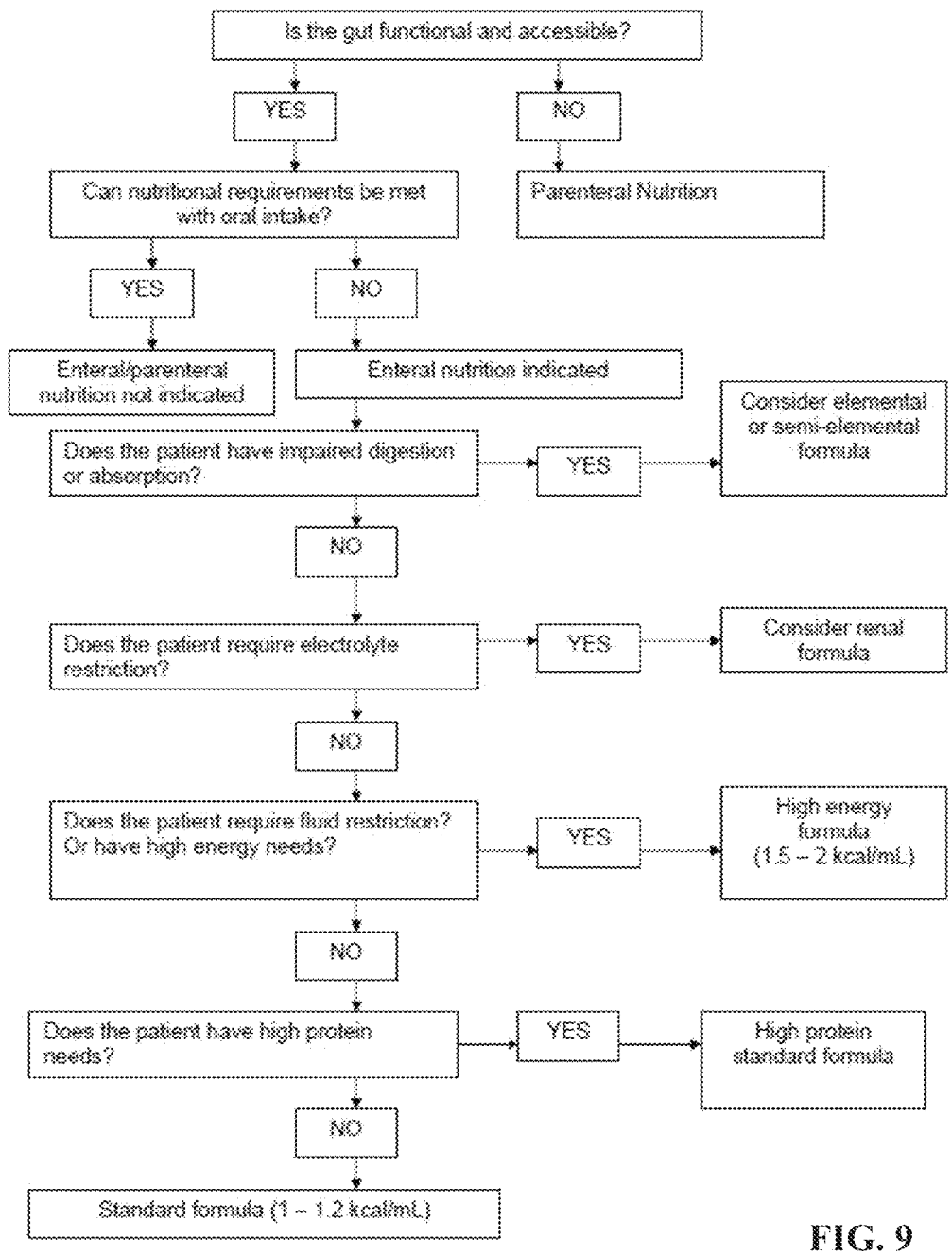

Reference is now made to FIG. 9, which is a flowchart of an exemplary method for automatic generation of the personalized nutrition regimen, in accordance with some embodiments of the present invention. The method based on FIG. 9 may be implemented by processing 216 of control unit 214 executing code stored in program store 218, and/or by client terminal 226, and/or another server. Branch points based on the medical state of the patient, such as based on test results, diagnosis, patient medical history, use of medications, and physical exam findings, and/or other data stored in patient medical records may be automatically (or manually) obtained by accessing medical records 222A. The personalized nutrition regimen may be selected based on data, for example, the table of FIG. 10, which may be locally stored in data repository 220, and/or accessed from a remote server.

Reference is now made to FIG. 11, which is a dataflow diagram for dynamic adjustment of the rate of fluid delivered to the stomach of the patient according to the calculated gastric emptying rate using the systems and/or methods described herein, in accordance with some embodiments of the present invention. At 1102, the desired feeding rate may be entered manually by a user (e.g., using GUI 232) and/or automatically selected by software (e.g., by accessing a database and/or using an equation). At 1104, a flow controller adjusts the flow rate of the fluid entering the stomach based on flow rate data collected by flow sensor 1106, to achieve desired feed rate 1102. The physiology of the stomach 1108 affects the actual gastric emptying rate of food 1110 (i.e., actual rate at which the stomach empties itself into the small intestine), for example, due to a disturbance, such as sedatives, surgery, and/or infection. Level sensors 1112 detect the level and/or volume of the fluid in the stomach. A supervisory feeding rate processor 1114 calculates the gastric emptying rate. The gastric emptying rate is compared to desired feed rate 1102 and/or to the measured fluid level in the stomach. Instructions to adjust the flow rate of the fluid entering the stomach are automatically generated and transmitted to flow control 1104 for dynamic adjustment of the rate of fluid entering the stomach.

Essentially the system described by FIG. 11 is a two level feedback control system with inner loop controlled by a flow sensor feedback and a supervisory control loop controlled by the tube mounted level sensors. Set point is provided by an operator or a nutrition algorithm as explained herein.

Reference is now made to FIG. 12, which is a flowchart of another method for dynamic adjustment of the rate of fluid delivered to the stomach of the patient using the systems and/or methods described herein, in accordance with some embodiments of the present invention. At 1202, a meal plan based on fluids delivered using a tube to the stomach of the patient is selected, manually and/or automatically, for example, using the suggested personalized nutrition regimen instruction code and/or method described herein. At 1204, fluid is delivered to the patient according to the selected nutrition regimen, using the systems and/or methods described herein. At 1206, the stomach sensors detect a pattern indicative of the level of fluid in the stomach. At 1208, when the level of fluid in the stomach is below a requirement indicating that there is additional room in the stomach (e.g., without increased risk of aspiration pneumonia), the feeding continues as planned. At 1210, when the level of fluid in the stomach is above the requirement (e.g., increased risk of aspiration pneumonia, decreased intestinal motility), a nurse may be alerted, for example, by sending a wireless message to a mobile device (e.g., Smartphone, tablet) of the nurse. Instructions may be automatically generated to slow down or stop the fluid delivery. The control unit monitors the level of fluid in the stomach until the fluid level falls below the requirement. The control unit signals the flow control mechanism to resume feeding. The control unit generates instructions to dynamically adjust the flow rate of fluid being delivered to the stomach, optionally based on the monitored level of fluid, the calculated gastric emptying rate, and/or the nutrition regiment. The generated instructions may include instructions to increase the feeding rate 1212, continue with the current feeding rate 1214, or decrease the feeding rate 1216.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant systems and methods will be developed and the scope of the terms stomach sensor, and fluid flow sensor are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for calculating a gastric emptying rate from a stomach lumen into a small intestine of a patient, comprising:
using at least one processor for executing the following during an enteral tube feeding of a stomach of the patient by a feeding mechanism:
receiving a personalized nutrition plan including a target fluid delivery rate;
performing the enteral tube feeding according to the target fluid delivery rate;
analyzing outputs of at least one stomach sensor located within the stomach for detecting a stop feeding condition;
pausing the enteral tube feeding in response to a detection of the stop feeding condition;
after a predefined period of time, restarting the enteral tube feeding until the stop condition is redetected by an analysis of outputs of the at least one stomach sensor which are obtained after the restarting;
calculating the gastric emptying rate based on an amount of feeding content delivered during a period between the restarting and the redetection;
adapting the target fluid delivery rate of the feeding mechanism for the enteral tube feeding according to the calculated gastric emptying rate; and
presenting a suggestion to administer gastroprokinetic medication on a display when the target fluid delivery rate included in the received personalized nutrition plan is higher than the calculated gastric emptying rate based on a tolerance.

2. A computer implemented method for calculating a gastric emptying rate from a stomach lumen into a small intestine of a patient, comprising:
using at least one processor for executing the following during an enteral tube feeding of a stomach of the patient by a feeding mechanism:
receiving a personalized nutrition plan including a target fluid delivery rate;
performing the enteral tube feeding according to the target fluid delivery rate;
analyzing outputs of at least one stomach sensor located within the stomach for detecting a stop feeding condition;
pausing the enteral tube feeding in response to a detection of the stop feeding condition;
after a predefined period of time, restarting the enteral tube feeding until the stop condition is redetected by an analysis of outputs of the at least one stomach sensor which are obtained after the restarting;
calculating the gastric emptying rate based on an amount of feeding content delivered during a period between the restarting and the redetection; and
adapting the target fluid delivery rate of the feeding mechanism for the enteral tube feeding according to the calculated gastric emptying rate;
wherein the target fluid delivery rate includes different values defined according to a time of day.

3. The method of claim 2, further comprising:
presenting within a GUI presented on a display at least one field for receiving a user input indicative of at least one patient parameter;
calculating a plurality of feeding options according to the at least one patient parameter;
presenting the plurality of feeding options within the GUI;
receiving, using the GUI, a user selection of at least one of the plurality of feeding options; and
calculating the personalized nutrition plan and the target fluid delivery rate based on the received selection.

4. The method of claim 3, wherein the at least one patient parameter includes at least one member selected from the group consisting of: gender, age, height, weight, diet restrictions, acute medical condition, and chronic medical condition.

5. The method of claim 3, wherein the plurality of feeding options include at least one member selected from the group consisting of: calories, protein amount, method of calculation, and available formulas.

6. The method of claim 2, further comprising transmitting an alert message for presentation on a display of a mobile device when the target fluid delivery rate included in the received personalized nutrition plan is different than the calculated gastric emptying rate.

7. The method of claim 2, wherein fluid is delivered during the period between the restarting and the redetection according to the target fluid delivery rate, and the gastric emptying rate is calculated based on the fluid delivered during the period between the restarting and the redetection.

8. The method of claim 2, wherein the predefined period of time is selected to correspond to an estimated amount of time expected for the stomach of the patient to empty itself of a fluid meal.

9. The method of claim 2, wherein the predefined period of time is automatically determined based on an analysis of signals received from stomach activity sensors located in the stomach indicative of a stomach emptying event.

10. The method of claim 9, wherein the stomach emptying event is automatically detected by identifying at least one signal pattern correlated with stomach peristalsis activity associated with the stomach emptying event.

11. A computer implemented method for calculating a gastric emptying rate from a stomach lumen into a small intestine of a patient, comprising:
using at least one processor for executing the following during an enteral tube feeding of a stomach of the patient by a feeding mechanism:
analyzing outputs of at least one stomach sensor located within the stomach for detecting a stop feeding condition;
pausing the enteral tube feeding in response to a detection of the stop feeding condition;
after a predefined period of time, restarting the enteral tube feeding until the stop condition is redetected by an analysis of outputs of the at least one stomach sensor which are obtained after the restarting;
calculating the gastric emptying rate based on an amount of feeding content delivered during a period between the restarting and the redetection; and
adapting the target fluid delivery rate of the feeding mechanism for the enteral tube feeding according to the calculated gastric emptying rate;
wherein the calculating is performed using the equation:

$$q=Q/(T+t)$$

wherein:
q denotes the gastric emptying rate;
Q denotes the volume of fluid needed to fill the stomach from a first sensor Z1 representing a low fluid level to a second sensor Z2 representing a high fluid level;

T denotes the elapsed gastric emptying time from fluid level Z2 to Z1; and t denotes the filling make up time.

12. The method of claim 11, wherein:

when the fluid reaches Z2 feeding is paused for a time period T, then feeding is resumed until level Z2 is reached and the time t is measured.

13. A system for calculating a gastric emptying rate from a stomach lumen into a small intestine of a patient, comprising:

a control unit, comprising:
an output interface;
a feeding mechanism interface;
a sensor interface that receives at least one signal from at least one stomach sensor located within a stomach lumen of a patient;
a program for storing code;
a processor coupled to the sensor interface, the output interface, the feeding mechanism interface, and the program store for implementing the stored code, the code comprising:
code to analyzing outputs of at least one stomach sensor located within the stomach for detecting a stop feeding condition, pause enteral tube feeding in response to a detection of the stop feeding condition, after a predefined period of time restart the enteral tube feeding until the stop condition is redetected by an analysis of outputs of the at least one stomach sensor which are obtained after the restarting, calculate the gastric emptying rate based on an amount of feeding content delivered during a period between the restarting and the redetection; and instruct the feeding mechanism to adapt a feeding rate of the enteral tube feeding according to the calculated gastric emptying rate;

wherein the calculating is performed using the equation:

$$q=Q/(T+t)$$

wherein:

q denotes the gastric emptying rate;

Q denotes the volume of fluid needed to fill the stomach from a first sensor Z1 representing a low fluid level to a second sensor Z2 representing a high fluid level;

T denotes the elapsed gastric emptying time from fluid level Z2 to Z1; and t denotes the filling make up time.

14. The system of claim 13, wherein the at least one stomach sensors include at least one impedance sensor and the at least one signal includes at least one impedance measurement.

15. The system of claim 13, wherein the at least one stomach sensor includes at least one fluid sensor disposed along a distal end portion of an enteral feeding tube positioned in the stomach of the patient such that the at least one fluid sensor is located within the stomach in proximity to the lower esophageal sphincter, and the at least one signal denotes the presence of fluid in proximity to the respective sensor at a respective position along the tube.

16. The system of claim 13, further comprising:

a graphical user interface (GUI) application installed on a client terminal in communication with the control unit through a network interface, the GUI application allowing a user to enter at least one patient parameter;

wherein the code further comprising:

code to determine a personalized nutrition plan including a target fluid delivery rate based on the at least one patient parameter, and code to compare the target fluid delivery rate to the calculated gastric emptying rate, and adjust the personalized nutrition plan by adjusting the target fluid delivery rate according to the comparison.

* * * * *